US012478488B2

(12) United States Patent
Richter et al.

(10) Patent No.: US 12,478,488 B2
(45) Date of Patent: Nov. 25, 2025

(54) HELICAL STENT WITH ENHANCED CRIMPING

(71) Applicant: Medinol Ltd., Tel Aviv (IL)

(72) Inventors: Yoram Richter, Ramat Hasharon (IL); Igor Belobrovy, Petah-Tiqwa (IL)

(73) Assignee: MEDINOL LTD., Tel Aviv (IL)

( * ) Notice: Subject to any disclaimer, the term of this patent is extended or adjusted under 35 U.S.C. 154(b) by 273 days.

(21) Appl. No.: 16/794,359

(22) Filed: Feb. 19, 2020

(65) Prior Publication Data

US 2021/0251783 A1 Aug. 19, 2021

(51) Int. Cl.

*A61F 2/88* (2006.01)
*A61F 2/915* (2013.01)
*A61F 2/07* (2013.01)
*A61F 2/95* (2013.01)

(52) U.S. Cl.

CPC *A61F 2/88* (2013.01); *A61F 2/07* (2013.01); *A61F 2002/91575* (2013.01); *A61F 2/9522* (2020.05); *A61F 2250/001* (2013.01); *A61F 2250/0067* (2013.01)

(58) Field of Classification Search

CPC .......... A61F 2/88
See application file for complete search history.

(56) References Cited

U.S. PATENT DOCUMENTS 3,223,032 A 12/1965 Boardman et al.
3,986,867 A 10/1976 Masumoto et al.
4,017,911 A 4/1977 Kafesjian et al.
(Continued)

FOREIGN PATENT DOCUMENTS

AU 2002352871 9/2003
AU 2003261912 3/2004
(Continued)

OTHER PUBLICATIONS

Horton et al., "Biomedical Potential of a Zirconium-Based Bulk Metallic Glass" Mat. Res. Soc. Symp. Proc. vol. 754, Materials Research Society, Feb. 14, 2003, http://www.ornl.gov/webworks/cppr/y2001/pres/116372.pdf.
(Continued)

*Primary Examiner* — Jacqueline Woznicki
(74) *Attorney, Agent, or Firm* — Davis Graham & Stubbs LLP

(57) ABSTRACT

The invention is directed to an endovascular device having an undulating pattern of struts and loops, where at least one strut has a bend in the crimped profile for reducing the compressed diameter. The strut configuration comprises one or more bent sections facing in opposite convex and concave orientations, thereby creating a space or hollow for an oppositely aligned portion of the device to nestle therein as the device is compressed. The undulating pattern may be staggered such that adjacent loops in the helical direction are axially offset with respect to a perpendicular axis perpendicular to the lengthwise direction, where a loop may be positioned to align with an adjacent strut in the helical direction. The device may include struts of varying lengths which may contribute to an enlarged expanded diameter of the device. The bent strut design of the crimped profile may be used with any endovascular strut design.

29 Claims, 16 Drawing Sheets

(56) References Cited

U.S. PATENT DOCUMENTS 4,142,571 A 3/1979 Narasimhan
4,144,058 A 3/1979 Chen et al.
4,185,383 A 1/1980 Heimke et al.
4,281,706 A 8/1981 Liebermann et al.
4,409,041 A 10/1983 Datta et al.
4,440,585 A 4/1984 Kanehira
4,473,401 A 9/1984 Masumoto et al.
4,481,001 A 11/1984 Graham et al.
4,489,773 A 12/1984 Miller
4,614,221 A 9/1986 Masumoto
4,655,771 A 4/1987 Wallsten
4,733,665 A 3/1988 Palmaz
4,755,593 A 7/1988 Lauren
4,760,849 A 8/1988 Kropf
4,762,128 A 8/1988 Rosenbluth
4,800,882 A 1/1989 Gianturco
4,802,776 A 2/1989 Miyazawa et al.
4,856,516 A 8/1989 Hillstead
4,886,062 A 12/1989 Wiktor
4,969,458 A 11/1990 Wiktor
5,019,090 A 5/1991 Pinchuk
5,037,377 A 8/1991 Alonso
5,045,637 A 9/1991 Sato et al.
5,102,417 A 4/1992 Palmaz
5,104,404 A 4/1992 Wolff
5,116,360 A 5/1992 Pinchuk et al.
5,116,365 A 5/1992 Hillstead
5,122,154 A 6/1992 Rhodes
5,123,917 A 6/1992 Lee
5,128,214 A 7/1992 Takayanagi et al.
5,133,732 A 7/1992 Wiktor
5,135,536 A 8/1992 Hillstead
5,161,547 A 11/1992 Tower
5,195,984 A 3/1993 Schatz
5,282,824 A 2/1994 Gianturco
5,292,331 A 3/1994 Boneau
5,314,472 A 5/1994 Fontaine
5,368,659 A 11/1994 Peker et al.
5,370,683 A 12/1994 Fontaine
5,381,856 A 1/1995 Fujikura et al.
5,383,892 A 1/1995 Cardon et al.
5,393,594 A 2/1995 Koyfman et al.
5,405,377 A 4/1995 Cragg
5,421,919 A 6/1995 Roman
5,443,496 A 8/1995 Schwartz et al.
5,449,373 A 9/1995 Pinchasik et al.
5,464,438 A 11/1995 Menaker
5,510,077 A 4/1996 Dinh et al.
5,514,176 A 5/1996 Bosley
5,527,337 A 6/1996 Stack et al.
5,549,663 A 8/1996 Cottone et al.
5,554,181 A 9/1996 Das
5,554,182 A 9/1996 Dinh et al.
5,556,413 A 9/1996 Lam
5,562,729 A 10/1996 Purdy et al.
5,571,166 A 11/1996 Dinh et al.
5,575,818 A 11/1996 Pinchuk
5,591,197 A 1/1997 Orth et al.
5,591,198 A 1/1997 Boyle et al.
5,591,223 A 1/1997 Lock et al.
5,591,224 A 1/1997 Lock et al.
5,595,571 A 1/1997 Jaffe et al.
5,603,721 A 2/1997 Lau et al.
5,609,627 A 3/1997 Goicoechea et al.
5,618,299 A 4/1997 Khosravi et al.
5,626,604 A 5/1997 Cottone
5,628,785 A 5/1997 Scwartz et al.
5,632,771 A 5/1997 Boatman et al.
5,636,641 A 6/1997 Fariabi
5,653,747 A 8/1997 Dereume
5,672,169 A 9/1997 Verbeek
5,674,278 A 10/1997 Boneau
5,693,084 A 12/1997 Chuter et al.
5,693,085 A 12/1997 Buirge et al.
5,696,207 A 12/1997 Vargo et al.
5,716,396 A 2/1998 Williams, Jr.
5,720,776 A 2/1998 Chuter et al.
5,720,777 A 2/1998 Jaffe et al.
5,723,003 A 3/1998 Winston et al.
5,725,573 A 3/1998 Dearnaley et al.
5,728,150 A 3/1998 McDonald et al.
5,733,303 A * 3/1998 Israel .................... A61F 2/91
623/1.15
5,755,781 A 5/1998 Jayaraman
5,769,884 A 6/1998 Solovay
5,779,732 A 7/1998 Amundson
5,782,905 A 7/1998 Richter
5,788,626 A 8/1998 Thompson
5,797,443 A 8/1998 Lin et al.
5,800,456 A 9/1998 Maeda et al.
5,800,507 A 9/1998 Scwartz et al.
5,800,508 A 9/1998 Goicoechea et al.
5,800,509 A 9/1998 Boneau
5,807,404 A 9/1998 Richter
5,810,872 A * 9/1998 Kanesaka ................ A61F 2/91
606/198
5,817,152 A 10/1998 Birdsall et al.
5,824,037 A 10/1998 Fogarty et al.
5,824,046 A 10/1998 Smith et al.
5,824,052 A 10/1998 Khosravi et al.
5,836,964 A 11/1998 Richter et al.
5,836,966 A 11/1998 St. Germain
5,843,120 A 12/1998 Israel et al.
5,843,180 A 12/1998 Jaffe et al.
5,843,181 A 12/1998 Jaffe et al.
5,849,034 A 12/1998 Schwartz
5,851,228 A 12/1998 Pinheiro
5,855,597 A 1/1999 Jayaraman
5,855,600 A 1/1999 Alt
5,865,723 A 2/1999 Love
5,879,381 A 3/1999 Moriuchi et al.
5,879,382 A 3/1999 Boneau
5,891,190 A 4/1999 Boneau
5,895,407 A 4/1999 Jayaraman
5,895,419 A 4/1999 Tweden et al.
5,899,934 A 5/1999 Amundson et al.
5,902,332 A 5/1999 Schatz
5,913,895 A 6/1999 Burpee et al.
5,913,897 A 6/1999 Corso et al.
5,922,020 A 7/1999 Klein et al.
5,922,021 A * 7/1999 Jang ...................... A61F 2/91
623/1.15
5,925,061 A 7/1999 Ogi et al.
5,928,279 A 7/1999 Shannon et al.
5,931,867 A 8/1999 Haindl
5,938,697 A 8/1999 Killion et al.
5,955,145 A 9/1999 Kalvala et al.
5,964,770 A 10/1999 Flomenblit et al.
5,997,575 A 12/1999 Whitson et al.
5,997,973 A 12/1999 Bianca, Jr.
6,010,530 A 1/2000 Goicoechea
6,013,091 A 1/2000 Ley et al.
6,013,854 A 1/2000 Moriuchi
6,017,365 A * 1/2000 Von Oepen .............. A61F 2/88
623/1.15
6,027,525 A 2/2000 Suh et al.
6,027,527 A 2/2000 Asano et al.
6,042,605 A 3/2000 Martin et al.
6,042,606 A 3/2000 Frantzen
6,053,941 A 4/2000 Lindberg et al.
6,059,808 A 5/2000 Boussignac et al.
6,080,192 A 6/2000 Demopulos et al.
6,096,070 A 8/2000 Ragheb et al.
6,099,561 A * 8/2000 Alt ....................... A61F 2/915
623/1.34
6,120,534 A 9/2000 Ruiz
6,120,847 A 9/2000 Yang et al.
6,123,721 A * 9/2000 Jang ...................... A61F 2/91
623/1.15
6,132,461 A 10/2000 Thompson
6,139,573 A 10/2000 Sogard et al.
6,159,237 A 12/2000 Alt et al.
6,159,239 A 12/2000 Greenhalgh
6,162,537 A 12/2000 Martin et al.

(56) References Cited

U.S. PATENT DOCUMENTS 6,179,868 B1 1/2001 Burpee et al.
6,183,353 B1 2/2001 Frantzen
6,187,034 B1 2/2001 Frantzen
6,187,095 B1 2/2001 Labrecque et al.
6,190,403 B1 2/2001 Fischell et al.
6,190,406 B1 * 2/2001 Duerig .................... A61F 2/91 623/1.15
6,190,407 B1 2/2001 Ogle et al.
6,193,747 B1 * 2/2001 von Oepen ............... A61F 2/91 623/1.15
6,197,048 B1 3/2001 Richter
6,197,049 B1 3/2001 Shaolian et al.
6,221,098 B1 4/2001 Wilson et al.
6,224,625 B1 5/2001 Javaraman
6,231,598 B1 5/2001 Berry et al.
6,238,401 B1 5/2001 Richter
6,240,615 B1 6/2001 Kimes et al.
6,241,762 B1 6/2001 Shanley
6,251,059 B1 6/2001 Apple et al.
6,251,134 B1 6/2001 Alt et al.
6,258,116 B1 7/2001 Hojeibane
6,258,117 B1 7/2001 Camrud et al.
6,264,689 B1 7/2001 Colgan et al.
6,273,910 B1 8/2001 Limon
6,287,333 B1 9/2001 Appling et al.
6,299,604 B1 10/2001 Ragheb et al.
6,299,755 B1 10/2001 Richter
6,309,411 B1 10/2001 Lashinski et al.
6,312,459 B1 11/2001 Huang et al.
6,315,794 B1 11/2001 Richter
6,319,277 B1 11/2001 Rudnick et al.
6,325,825 B1 12/2001 Kula et al.
6,331,188 B1 12/2001 Lau et al.
6,331,189 B1 * 12/2001 Wolinsky .................. A61F 2/91 623/1.15
6,334,868 B1 1/2002 Ham
6,340,367 B1 1/2002 Stinson et al.
6,344,053 B1 2/2002 Boneau
6,348,065 B1 2/2002 Brown et al.
6,352,552 B1 * 3/2002 Levinson ................. A61F 2/91 623/1.15
6,355,039 B1 3/2002 Troussel et al.
6,355,059 B1 3/2002 Richter et al.
6,364,904 B1 4/2002 Smith et al.
6,383,213 B2 5/2002 Wilson et al.
6,387,120 B2 5/2002 Wilson et al.
6,398,803 B1 6/2002 Layne
6,409,753 B1 6/2002 Brown et al.
6,416,538 B1 7/2002 Ley et al.
6,428,569 B1 8/2002 Brown
6,440,162 B1 8/2002 Cox et al.
6,464,719 B2 10/2002 Jayaraman
6,471,980 B2 10/2002 Sirhan et al.
6,475,232 B1 11/2002 Babbs et al.
6,478,815 B1 11/2002 Alt
6,485,508 B1 11/2002 McGuiness
6,503,270 B1 1/2003 Richter et al.
6,505,654 B1 1/2003 Andersen et al.
6,506,211 B1 1/2003 Skubitz et al.
6,506,408 B1 1/2003 Palasis
6,511,505 B2 1/2003 Cox et al.
6,527,801 B1 3/2003 Dutta
6,530,934 B1 3/2003 Jacobsen et al.
6,530,950 B1 3/2003 Alvarado et al.
6,540,774 B1 4/2003 Cox
6,540,775 B1 4/2003 Fischell et al.
6,558,414 B2 5/2003 Layne
6,562,065 B1 5/2003 Shanley
6,565,507 B2 5/2003 Kamata et al.
6,569,180 B1 5/2003 Sirhan et al.
6,572,648 B1 6/2003 Klumb et al.
6,579,310 B1 6/2003 Cox et al.
6,579,314 B1 6/2003 Lombardi
6,602,226 B1 8/2003 Smith et al.
6,602,281 B1 8/2003 Klein
6,602,282 B1 8/2003 Yan et al.
6,605,107 B1 8/2003 Klein
6,607,554 B2 8/2003 Dang et al.
6,610,086 B1 8/2003 Kock et al.
6,613,079 B1 * 9/2003 Wolinsky .................. A61F 2/95 623/1.15
6,613,084 B2 9/2003 Yang
6,629,994 B2 10/2003 Gomez et al.
6,635,083 B1 * 10/2003 Cheng ...................... A61F 2/91 623/1.15
6,638,301 B1 10/2003 Chandrasekaran et al.
6,645,237 B2 11/2003 Klumb et al.
6,645,240 B2 11/2003 Yee
6,648,911 B1 11/2003 Sirhan et al.
6,656,218 B1 12/2003 Denardo et al.
6,656,220 B1 12/2003 Gomez et al.
6,663,661 B2 12/2003 Boneau
6,663,664 B1 12/2003 Pacetti
6,673,102 B1 1/2004 Vonesh et al.
6,673,106 B2 1/2004 Mitelberg et al.
6,699,278 B2 3/2004 Fischell et al.
6,706,061 B1 3/2004 Fischell et al.
6,709,453 B2 3/2004 Pinchasik et al.
6,712,844 B2 3/2004 Pacetti
6,723,119 B2 * 4/2004 Pinchasik ................ A61F 2/91 623/1.15
6,730,117 B1 5/2004 Tseng et al.
6,733,536 B1 5/2004 Gellman
6,736,844 B1 5/2004 Glatt et al.
6,749,629 B1 * 6/2004 Hong ....................... A61F 2/91 623/1.15
6,767,418 B1 7/2004 Zhang et al.
6,770,087 B2 8/2004 Layne
6,790,298 B2 9/2004 Johnson et al.
6,821,292 B2 11/2004 Pazienza et al.
6,827,733 B2 12/2004 Boneau
6,863,757 B1 3/2005 Gonzalez et al.
6,866,805 B2 3/2005 Hong et al.
6,866,860 B2 3/2005 Nathan
6,899,727 B2 5/2005 Armstrong et al.
6,911,040 B2 6/2005 Johnson
6,962,604 B2 11/2005 Hijkema
7,037,330 B1 5/2006 Rivelli et al.
7,060,093 B2 6/2006 Dang et al.
7,108,714 B1 9/2006 Becker
7,112,293 B2 9/2006 Dubson et al.
7,141,062 B1 * 11/2006 Pinchasik ............... A61F 2/915 623/1.15
7,163,555 B2 1/2007 Dinh
7,176,344 B2 2/2007 Gustafson et al.
7,179,285 B2 * 2/2007 Ikeuchi .................... A61F 2/91 623/1.15
7,185,677 B2 3/2007 Houston et al.
7,244,116 B2 7/2007 Dubson et al.
D553,746 S * 10/2007 Fliedner ................. A61F 2/915 D24/155
7,329,277 B2 2/2008 Addonizio et al.
7,360,542 B2 4/2008 Nelson et al.
7,404,823 B2 * 7/2008 Gregorich ................ A61F 2/91 623/1.15
7,441,559 B2 10/2008 Nelson et al.
7,534,258 B2 * 5/2009 Gomez .................... A61F 2/91 623/1.17
7,540,881 B2 6/2009 Meyer et al.
7,637,939 B2 12/2009 Tischler
7,722,578 B2 5/2010 Arney et al.
7,722,661 B2 5/2010 Lenz et al.
7,763,064 B2 7/2010 Pinchasik
7,846,198 B2 12/2010 Hogendijk
7,887,584 B2 2/2011 Richter
7,901,448 B2 3/2011 Leopold et al.
7,914,568 B2 3/2011 Cully et al.
7,922,756 B2 4/2011 Lenz et al.
7,955,387 B2 6/2011 Richter
7,985,251 B2 * 7/2011 Ikeuchi .................... A61F 2/91 623/1.15
8,070,792 B2 * 12/2011 Gregorich ................ A61F 2/91 623/1.15

(56) References Cited

U.S. PATENT DOCUMENTS 8,236,043 B2 8/2012 Caro et al.
8,328,865 B2 12/2012 Bales et al.
8,382,821 B2 2/2013 Richter
8,460,364 B2 6/2013 Cottone et al.
8,496,703 B2 7/2013 Richter
8,882,824 B2* 11/2014 Kim ........................ A61F 2/915 623/1.15
9,039,755 B2 5/2015 Richter
9,155,639 B2 10/2015 Richter
9,456,910 B2 10/2016 Richter
9,603,731 B2 3/2017 Richter
9,622,888 B2 4/2017 Armstrong et al.
9,707,110 B2 7/2017 McDermott et al.
10,363,152 B2 7/2019 Richter
2001/0020184 A1 9/2001 Dehdashtian et al.
2001/0032009 A1 10/2001 Layne et al.
2001/0044647 A1 11/2001 Pinchuk et al.
2001/0047199 A1* 11/2001 Wijay ..................... A61F 2/915 623/1.15
2001/0053930 A1 12/2001 Kugler et al.
2001/0056298 A1 12/2001 Brown et al.
2002/0004677 A1 1/2002 Jayaraman
2002/0007212 A1* 1/2002 Brown .................... A61F 2/915 623/1.16
2002/0046783 A1 4/2002 Johnson et al.
2002/0049488 A1 4/2002 Boneau
2002/0049489 A1 4/2002 Herweck et al.
2002/0049490 A1 4/2002 Pollock
2002/0049492 A1 4/2002 Lashinski et al.
2002/0052649 A1 5/2002 Greenhalgh
2002/0055770 A1 5/2002 Doran et al.
2002/0068969 A1 6/2002 Shanley et al.
2002/0081732 A1 6/2002 Bowlin et al.
2002/0082680 A1 6/2002 Shanley et al.
2002/0082682 A1 6/2002 Barclay et al.
2002/0084178 A1 7/2002 Dubson et al.
2002/0095206 A1* 7/2002 Addonizio ................ A61F 2/91 623/1.15
2002/0103529 A1 8/2002 Pinchasik et al.
2002/0107560 A1 8/2002 Richter
2002/0111669 A1* 8/2002 Pazienza ................... A61F 2/91 623/1.15
2002/0116044 A1 8/2002 Cottone et al.
2002/0116049 A1 8/2002 Girton et al.
2002/0120327 A1 8/2002 Cox et al.
2002/0123798 A1 9/2002 Burgermeister
2002/0138136 A1 9/2002 Chandresekaran et al.
2002/0161319 A1 10/2002 Matsumoto et al.
2002/0162605 A1 11/2002 Horton, Jr. et al.
2002/0165603 A1 11/2002 Thornton et al.
2002/0177893 A1 11/2002 Brown et al.
2003/0017208 A1 1/2003 Ignatious et al.
2003/0028245 A1 2/2003 Barclay et al.
2003/0040803 A1 2/2003 Rioux et al.
2003/0045926 A1 3/2003 Pinchasik
2003/0050691 A1 3/2003 Shifrin et al.
2003/0069633 A1 4/2003 Richter et al.
2003/0083646 A1 5/2003 Sirhan et al.
2003/0100955 A1 5/2003 Greenawalt et al.
2003/0120197 A1 6/2003 Kaneko et al.
2003/0130721 A1 7/2003 Martin et al.
2003/0208260 A1 11/2003 Lau et al.
2003/0211135 A1 11/2003 Greenhalgh et al.
2003/0212449 A1 11/2003 Cox
2004/0007323 A1 1/2004 Bevins, III et al.
2004/0013834 A1 1/2004 Bonk et al.
2004/0030377 A1* 2/2004 Dubson .................. D04H 1/728 623/1.13
2004/0039439 A1 2/2004 Gomez et al.
2004/0044401 A1* 3/2004 Bales ...................... A61F 2/915 623/1.22
2004/0064180 A1 4/2004 Boneau
2004/0072124 A1 4/2004 Kaufman et al.
2004/0073291 A1* 4/2004 Brown ...................... A61F 2/91 623/1.15
2004/0082989 A1 4/2004 Cook et al.
2004/0088043 A1 5/2004 Klein
2004/0098095 A1 5/2004 Burnside et al.
2004/0102833 A1 5/2004 Girton et al.
2004/0106980 A1 6/2004 Solovay et al.
2004/0193251 A1 9/2004 Rudnick et al.
2004/0199242 A1 10/2004 Hong et al.
2004/0204751 A1 10/2004 Fischell et al.
2004/0230291 A1 11/2004 Richter
2004/0236402 A1 11/2004 Layne
2004/0254419 A1 12/2004 Wang et al.
2004/0255096 A1 12/2004 Norman
2004/0260401 A1 12/2004 Crawley et al.
2004/0267349 A1 12/2004 Richter
2005/0033399 A1 2/2005 Richter
2005/0043782 A1 2/2005 Gomez et al.
2005/0084407 A1 4/2005 Myrick
2005/0107864 A1 5/2005 Hong et al.
2005/0113888 A1 5/2005 Jimenez et al.
2005/0131515 A1 6/2005 Cully et al.
2005/0182483 A1 8/2005 Osborne et al.
2005/0209679 A1 9/2005 Melsheimer
2005/0216076 A1 9/2005 Kveen et al.
2005/0233593 A1 10/2005 Brunet et al.
2005/0246010 A1 11/2005 Alexander et al.
2005/0261758 A1 11/2005 Rourke et al.
2005/0278019 A1 12/2005 Gregorich
2006/0030934 A1 2/2006 Hogendijk et al.
2006/0064154 A1* 3/2006 Bales ...................... A61F 2/844 623/1.15
2006/0122691 A1 6/2006 Richter
2006/0149386 A1 7/2006 Clarke et al.
2006/0178727 A1 8/2006 Richter
2006/0195177 A1 8/2006 Kaufmann et al.
2006/0246210 A1 11/2006 Iki et al.
2007/0026132 A1 2/2007 Williams et al.
2007/0073383 A1 3/2007 Yip et al.
2007/0150046 A1 6/2007 Meyer et al.
2007/0208409 A1 9/2007 Quigley
2007/0219618 A1 9/2007 Cully et al.
2007/0219642 A1 9/2007 Richter
2007/0239264 A1 10/2007 Fliedner
2007/0250148 A1 10/2007 Perry et al.
2007/0269936 A1 11/2007 Tanaka et al.
2008/0097579 A1* 4/2008 Shanley .................... A61F 2/91 623/1.16
2008/0097582 A1 4/2008 Shanley et al.
2008/0215129 A1 9/2008 Venturelli et al.
2008/0221664 A1 9/2008 Bales et al.
2008/0319534 A1 12/2008 Birdsall et al.
2008/0319535 A1 12/2008 Craven et al.
2009/0012525 A1 1/2009 Buehlmann et al.
2009/0036976 A1 2/2009 Beach et al.
2009/0062903 A1 3/2009 Pathak
2009/0210049 A1 8/2009 Thielen et al.
2009/0234433 A1 9/2009 Richter
2009/0259294 A1 10/2009 Cully et al.
2009/0264986 A1 10/2009 Bales et al.
2009/0306766 A1 12/2009 McDermott et al.
2010/0004725 A1 1/2010 Zipse et al.
2010/0016949 A1 1/2010 Wack
2010/0070024 A1 3/2010 Venturelli et al.
2010/0198333 A1 8/2010 Macatangay et al.
2010/0256735 A1 10/2010 Morales
2011/0004290 A1 1/2011 Bales et al.
2011/0125251 A1 5/2011 Cottone et al.
2011/0166641 A1 7/2011 Bales et al.
2011/0184507 A1 7/2011 Fischer, Jr. et al.
2011/0208288 A1 8/2011 Arbefeuille et al.
2011/0218615 A1 9/2011 Griswold
2011/0251668 A1 10/2011 Thompson et al.
2012/0265288 A1 10/2012 Jones et al.
2012/0303112 A1 11/2012 Armstrong et al.
2013/0090721 A1 4/2013 Bales et al.
2013/0306364 A1 11/2013 Suzuki et al.
2014/0135904 A1 5/2014 Rowe
2014/0358218 A1 12/2014 Mitsudo et al.

(56) References Cited

U.S. PATENT DOCUMENTS

| | | | |
|---|---|---|---|
| 2014/0379066 A1 | 12/2014 | Burpee et al. |
| 2015/0045874 A1 | 2/2015 | McMahon et al. |
| 2015/0250271 A1 | 9/2015 | Ogilvie |
| 2017/0196716 A1 | 7/2017 | Richter |

FOREIGN PATENT DOCUMENTS

| | | | |
|---|---|---|---|
| CA | 2092337 | | 9/1993 |
| CA | 2281775 | | 6/2000 |
| CA | 2370184 | | 10/2000 |
| DE | 195 12 066 | | 11/1996 |
| DE | 297 08 879 | | 7/1997 |
| DE | 197 53 123 | | 8/1999 |
| DE | 199 00 411 | | 7/2000 |
| DE | 199 57 063 | | 8/2001 |
| DE | 102 23 399 | | 6/2006 |
| EP | 0 364 787 | A1 | 4/1990 |
| EP | 0 480 667 | A1 | 4/1992 |
| EP | 0 623 354 | | 11/1994 |
| EP | 0 747 498 | A1 | 12/1996 |
| EP | 0 775 472 | A2 | 5/1997 |
| EP | 03 34 046 | B1 | 6/1997 |
| EP | 0 830 853 | | 3/1998 |
| EP | 0 888 757 | | 1/1999 |
| EP | 0 916 318 | | 5/1999 |
| EP | 0 958 794 | | 12/1999 |
| EP | 0 970 664 | | 1/2000 |
| EP | 0 876 216 | | 4/2000 |
| EP | 1 020 166 | | 7/2000 |
| EP | 1093771 | A2 | 4/2001 |
| EP | 1 129 673 | | 9/2001 |
| EP | 216 717 | A1 | 12/2001 |
| EP | 1161927 | | 12/2001 |
| EP | 148 843 | | 4/2003 |
| EP | 477 130 | | 11/2004 |
| EP | 937 184 | B1 | 8/2006 |
| EP | 834 606 | | 9/2007 |
| EP | 997 459 | | 12/2008 |
| EP | 526 905 | | 11/2012 |
| EP | 529 706 | | 12/2012 |
| EP | 3034047 | A1 | 6/2016 |
| FR | 758 253 | | 7/1998 |
| FR | 760 351 | | 9/1998 |
| JP | 61-106133 | | 5/1986 |
| JP | 01-121064 | | 5/1989 |
| JP | 02-047243 | | 2/1990 |
| JP | 02-057264 | | 2/1990 |
| JP | 2061036 | A | 3/1990 |
| JP | 2-174859 | | 7/1990 |
| JP | 03-009746 | | 1/1991 |
| JP | 07-080078 | | 3/1995 |
| JP | 07-124263 | | 5/1995 |
| JP | 07-188876 | | 7/1995 |
| JP | 07-188877 | | 7/1995 |
| JP | 07-265432 | | 10/1995 |
| JP | 08-243107 | | 9/1996 |
| JP | 2691074 | | 12/1997 |
| JP | 10-277082 | | 10/1998 |
| JP | 2000-167064 | | 6/2000 |
| JP | 2000-000297 | | 7/2000 |
| JP | 2001/231867 | | 8/2001 |
| JP | 2002-536055 | | 10/2002 |
| JP | 2003-520103 | | 7/2003 |
| JP | 2004-089580 | | 3/2004 |
| JP | 2004-261567 | | 9/2004 |
| JP | 2005-027840 | | 2/2005 |
| JP | 2005-522594 | | 7/2005 |
| JP | 2005-312584 | | 11/2005 |
| JP | 2007-167679 | | 7/2007 |
| JP | 2007-518520 | | 7/2007 |
| JP | 2007-527734 | | 10/2007 |
| JP | 2012524588 | | 10/2012 |
| NZ | 280547 | | 9/1998 |
| NZ | 285241 | | 3/1999 |
| NZ | 331532 | | 1/2000 |
| RU | 2234288 | C2 | 8/2004 |
| RU | 2460495 | C2 | 9/2012 |
| WO | WO 83/00997 | | 3/1983 |
| WO | WO 93/13825 | | 7/1993 |
| WO | WO 95/03010 | | 2/1995 |
| WO | WO 95/23876 | | 9/1995 |
| WO | WO 95/26695 | | 10/1995 |
| WO | WO 96/26689 | | 9/1996 |
| WO | WO 97/07889 | | 3/1997 |
| WO | WO 97/25937 | | 7/1997 |
| WO | WO 97/32544 | | 9/1997 |
| WO | WO 97/33534 | | 9/1997 |
| WO | WO 97/37617 | | 10/1997 |
| WO | WO 98/22159 | | 5/1998 |
| WO | WO 98/26732 | | 6/1998 |
| WO | WO 98/35634 | | 8/1998 |
| WO | WO 98/41169 | | 9/1998 |
| WO | WO 99/15108 | | 4/1999 |
| WO | WO 99/17680 | | 4/1999 |
| WO | WO 99/33410 | | 7/1999 |
| WO | WO 99/39660 | | 8/1999 |
| WO | WO 99/44543 | | 9/1999 |
| WO | WO 99/62431 | | 12/1999 |
| WO | WO 00/30563 | | 6/2000 |
| WO | WO 00/32138 | | 6/2000 |
| WO | WO 00/45741 | | 8/2000 |
| WO | WO 00/45743 | | 8/2000 |
| WO | WO 00/49971 | | 8/2000 |
| WO | WO 00/76423 | | 12/2000 |
| WO | WO 01/52771 | | 7/2001 |
| WO | WO 01/58504 | | 8/2001 |
| WO | WO 02/26279 | A1 | 4/2002 |
| WO | WO 02/34163 | | 5/2002 |
| WO | WO 02/35984 | | 10/2002 |
| WO | WO 03/026713 | | 4/2003 |
| WO | WO 03/057075 | | 7/2003 |
| WO | WO 03/057077 | | 7/2003 |
| WO | WO 03/082152 | | 10/2003 |
| WO | WO 03/087443 | | 10/2003 |
| WO | WO 04/016197 | | 2/2004 |
| WO | WO 2004/034931 | | 4/2004 |
| WO | WO 04/045454 | A | 6/2004 |
| WO | WO 2004/058100 | | 7/2004 |
| WO | WO 2004/110302 | | 12/2004 |
| WO | WO 2005/000152 | | 1/2005 |
| WO | WO 2005/034806 | A1 | 4/2005 |
| WO | WO 2005/058202 | | 6/2005 |
| WO | WO 2005/070337 | | 8/2005 |
| WO | WO 2005/072653 | | 8/2005 |
| WO | WO 2005/102220 | | 11/2005 |
| WO | WO 05/118971 | | 12/2005 |
| WO | WO 2006/014969 | | 2/2006 |
| WO | WO 2006/086069 | | 8/2006 |
| WO | WO 2007/080510 | | 7/2007 |
| WO | WO 07/105088 | | 9/2007 |
| WO | WO 2007/109007 | | 9/2007 |
| WO | WO 08/049045 | | 4/2008 |
| WO | WO 2008/062414 | | 5/2008 |
| WO | WO 2008/100783 | | 8/2008 |
| WO | WO 2008/117315 | | 10/2008 |
| WO | WO 2010/027494 | | 3/2010 |

OTHER PUBLICATIONS

Database WPI Week 20012 Derwent Publications Ltd., London GB; AN 2000-129595 XP002446760 / JP 2000-000297 A (Inoue A) Jan. 7, 2000.

Busch, R. et al., "On the Glass Forming Ability of Bulk Metallic Glass", Materials Science Forum vols. 235-238 (1997) pp. 327-336.

Cahn, R., "Atomic Transport in Amorphous Alloys: An Introduction", J.Vac. Sci, Technol. A (4(6), Nov./Dec. 1986.

Donaldson, J., "Metallic Glasses: A New Class of Electroplated Coatings", Surface Finishing, Jul. 1986.

Duwez, P. "A Typical Example of Metastability: Metallic Glasses", J. Vac. Sci. Technol. B1 (2) Apr.-Jun. 1983.

Fecht, H. et al., "Destabilization and Vitrification of Crystalline Matter", J. Non-Crystalline Solids, 117/118 (1990) 704-707.

(56) References Cited

OTHER PUBLICATIONS

Johnson, W.L. et al., “Electronic Structure of Metallic Glasses”, Glassy Metals: Magnetic, Chemical, and Structural Properties, CRC press, pp. 65-108.
Johnson, W.L., “Fundamental Aspects of Bulk Metallic Glass formation in Multicomponent Assays”, Materials Science Forum, vols. 225-227 (1996) pp. 35-50.
Johnson, W.L., “Bulk Metallic Glasses—A New Engineering Material”, current Opinion in Solid State & Materials Science, 1996, 1:383-386.
Johnson, W.L., “Mechanisms of Instability in Crystalline Alloys with Respect to Vitrification”, Journal of Less-Common Metals, 145 (1988) 63-80.
Kavesh, S., “Principles of Fabrication”, Metallic Glasses, Papers presented at a Seminar of the Materials Science Division of the American Society for Metals, Sep. 18 and 19, 1976.
Kukulka, D., “New Chill-block Melt Spinning Relations to Predict Ribbon Thickness”, J. Thermophysics, vol. 10, No. 3, Technical Notes, 1996.
Kung, K. T-Y., “Electrical Characteristics of Amorphous Molybdenum-Nickel Contacts to Silicon”, J.Appl. Phys., 55(10), May 15, 1984 pp. 3882-3885.
Liebermann, H., et al., “Technology of Amorphous Alloys”, ChemTech, Jun. 1987, pp. 363-367.
Liebermann, H.H., “The Dependence of the Geometry of Glassy Alloy Ribbons on the Chill Bock Melt-Spinning Process Parameters”, Materials Science and Engineering, 43 (1980) 203-210.
Takayama, S., et al., “The Analysis of Casting Conditions of Amorphous Alloys”, J. Appl. Phys. 50 (7), Jul. 1979, pp. 4962-4965.
Thakoor, A.P. et al., “Influence of the Microstructure on the Corrosion Behavior of Magnetron Sputter-Quenched Amorphous Metal Alloys”, J. Vac. Sci. Technol. A 1 (2), Apr.-Jun. 1983, pp. 520-523.
Williams, R.M. et al., “Corrosion Behavior of Magnetron Sputter-Deposited [MO0.6Rulo.4]B18 and M082B18 Amorphous Metal Films”, J. Electrochemical Soc., vol. 131 No. 12, pp. 2791-2794, Dec. 1984.
Zhu, M.F. et al., “Electrical Characteristics of Amorphous Ni36 W64 Contacts on SI”, Advanced Semiconductor Processing and Characterization of Electronic and Optical Materials, Proceedings of SPIE, vol. 463, Jan. 24-25, 1984.
Zhu, M. F., et al., “Investigation of Amorphous $W_{60}Zr_{40}$ Film as a Diffusion Barrier in Metallization Schemes”, Phys. Stat. Sol. (a) S6, 471 (1984).
“Technology: Hot Alloy” [online]. Forbes Magazine, Sep. 30, 2002[retrieved Feb. 19, 2003] Retrieved from the internet: <URL:www.forbes.com/global/2002/0930/128.html>.
“Innovative Material is Stronger than Titanium but can be formed like a Plastic” [online]. Jobwerx Manufacturing Network. [retrieved Feb. 19, 2003]. Retrieved from the internet: <URL:www.jobwerx.com/news/archives/LiquidmetalAlloys.com>.
“Liquidmetal Medical Devices” [online], Liquidmetal Technologies, [retrieved Feb. 20, 2003]. Retrieved from the internet: <URL:www.liquidmetal.com/applications/dsp.medical.asp>.
“Liquidmetal Technology Reborn in LMG” [online]. Golfweb, Jul. 31, 2002 [retrieved Feb. 20, 2003]. Retrieved from the internet: <URL:www.golfweb.com/u/cd/multi/0,1977m5564401,00.html>.
“Choosing the right suture material” [online], The Royal College of Surgeons of Edinburgh [retrieved Mar. 5, 2003]. Retrieved from the internet <URL: www.edu.rcsed.ac.uk/lectures/lt5.htm>.
“BBC health—Ask the Doctor—Heart Valves Replacement” [online]. BBC health homepage, Jul. 18, 2001. [retrieved Mar. 12, 2003]. Retrieved from the internet: <URL: www.bbc.co.uk/health/ask_doctor/heartvalve_replacement.shtml>.
“Artificial Organs Cardiovascular” [online]. National University of Singapore. [retrieved Mar. 12, 2003]. Retrieved from the internet <URL: www.scholars.nus.edu.sg/cpace/prosthesis/stein/cardio.html>.
“Heart replacement valves” [online]. Research Defense Society. [retrieved Mar. 12, 2003]. Retrieved from the internet: <URL: www.rds-online.org.uk/milestones/valves.html>.
“Material considerations in Replacement Heart Valves” [online]. Rose-Hulman Institute of Technology Fall 1996 [retrieved Mar. 12, 2003]. Retrieved from the internet: <URL: www.rose-hulman.edu/class/scheme/HTML/SiteMap/Undergraduate/StudentProjects/MaterialsStudentProjects/heart/heart.html>.
“The Physics Behind Artificial Heart Valves” [online]. Claire Carson, et al., Dec. 4, 2000 [retrieved Mar. 12, 2003] Retrieved from the internet: <URL: www.ipass.net/~tonyg/HeartValvesWeb.html>.
“Medical Dictionary—Artificial Heart Valve” [online]. Dr. Malcolm C. Brown, 2000 [retrieved on Mar. 12, 2003]. Retrieved from the internet: <URL: http://www.thebrowns23.freeserve.co.uk/entries/ARTIFICIAL_HEART_VALVE>.
Jostent Peripheral Stent Graft [online]. JOMED 2002, [retrieved Mar. 14, 2003]. Retrieved from the internet: <URL:www.jomed.com/products/jpsg/productinfo/jostent-psg.html>.
Devanathan, Deva, “Recent Advances in Titanium Wire Technology”, [online]. TP Orthodontics, Inc. Jan. 1999 [retrieved Mar. 15, 2003]. Retrieved from the internet: <URL:http://www.tportho.com/doctorsroom/whitepapers/pdf/titanium.pdf>.
“Dental Implants” [online]. Niagara Oral Surgery [retrieved on Mar. 17, 2003] <URL: www.niagaraoralsurgery.com/ser_implants.htm>.
“Lecture 11—Metals for Implantation”, [online]. Wayne State University, [retrieved Mar. 17, 2003]. Retrieved from the internet: <URL:http://ttb.eng.wayne.edu/~grimm/BME5370/Lect11Out.html>.
“Investment Materials” [online]. Guy’s, King’s College & St. Thomas’s Hospital Dental Institute, Dental Biomaterials Science, R. V. Curtis [retrieved Mar. 15, 2003]. Retrieved from the internet: <URL: http://r-curtis.umds.ac.uk/bds3a/investment%20materials%201.htm>.
“Metal Casting Alloys” [online]. Guy’s, King’s College & St. Thomas’s Hospital Dental Institute, Dental Biomaterials Science, R. V. Curtis [retrieved on Mar. 15, 2003]. Retrieved from the internet: <URL: http://r-curtis.umds.ac.uk/bds3a/BMCalloys.HTM>.
“Metals & Alloys” [online]. Guy’s, King’s College & St. Thomas’s Hospital Dental Institute, Dental Biomaterials Science, R.V. Curtis, [retrieved on Mar. 15, 2003]. Retrieved from the internet: <URL: http://r-curtis.umds.ac.uk/bds3a/metallurgy.HTM>.
“TP Original Wire: Development of a High-Performance Orthodontic Wire”, [online]. TP Orthodontics, Inc. 1998 [retrieved on Mar. 15, 2003]. Retrieved from the internet: <URL: http://www.tportho.com.br/doctorsroom/whitepapers/pdf/originalwire.pdf>.
“Metallic Glasses Bulk Up”, [online]. Mechanical Engineering Magazine, Jun. 1998. [retrieved on Mar. 21, 2003]. Retrieved from the internet: <URL:www.memagazine.org/backissues/june98/features/metallic/metallic.html>.
“Hasta La Vista, Titanium”, [online]. Business 2.0, Oct. 2002. [retrieved on Mar. 21, 2003]. Retrieved from the internet: <URL:www.business2.com/articles/mag/print/0,1643,43538,00.html>.
“New metal alloy is super strong”, [online]. You magazine. [retrieved on Mar. 21, 2003]. Retrieved on the internet: <URL:www.yo.com.au/news/1022.htm>.
“Lessons of the Björk-Shiley Heart Valve Failure, Mechanics of Heart Valves” [online]. University of Texas at Austin. [retrieved on Mar. 25, 2003]. Retrieved from the internet: <URL: www.me.utexas.edu/~uer/heartvalves/mechanics.html>.
Atzmon, M. et al., “Study of Amorphous Phases Formed by Solid-State Reaction in Elemental Composites”, Rapidly Quenched Metals, Proceedings of the Fifth International Conference on Rapidly Quenched Metals, Wüzburg, Germany, Sep. 3-7, 1984.
International Search Report and Written Opinion dated Oct. 28, 2020 for PCT Application No. PCT/IB2020/000165, 10 pages.

* cited by examiner

HELICAL STENT WITH ENHANCED CRIMPING

FIELD OF THE INVENTION

The invention relates generally to intraluminal endovascular devices, such as stents which are implanted into vessels within the body, for example blood vessels, in order to open vessels that were narrowed or blocked as a result of, for example, coronary artery disease (CAD), restore blood flow, and/or maintain the vessels' patency. More particularly, the invention relates to endovascular devices, including stents, having a reduced compressed or crimped profile and/or an enlarged expanded profile.

BACKGROUND OF THE INVENTION

Various stents are known in the art. Typically, stents are mesh-like metallic structures, tubular in shape, and are expandable from a smaller, unexpanded, diameter to a larger, expanded, diameter. For implantation, the stent is typically mounted on the distal part of a catheter with the stent being held on the catheter in a crimped, unexpanded diameter. Using a catheter guided by a guide-wire slidably extending therethrough, the unexpanded stent is delivered through the vascular or gastro-intestinal system to the intended implantation site, for example a blood vessel or a coronary artery. Once the stent is at the intended implantation site, it is expanded radially, typically either by a force, for example by inflating a balloon on the inside of the stent, or by allowing the stent to self-expand, for example by removing a sleeve from around a self-expanding stent thus allowing the stent to expand radially. In either case, the expanded stent resists the tendency of the vessel to re-narrow, thereby maintaining the vessel's patency.

Stents may be manufactured by laser cutting the stent pattern into a tube or a flat sheet of metal. In the latter case, the sheet is later rolled and fixed such as by welding, mechanical lock or otherwise, to form the tubular structure of the stent.

One type of stent is known as the helical or coiled stent. Such a stent design is described in, for example, U.S. Pat. Nos. 6,503,270 and 6,355,059, which are incorporated herein, in toto, by reference. This stent design is configured as a helical stent in which the coil is formed from a wound strip of cells, where the cells form a serpentine pattern comprising a series of bends formed from an alternating arrangement of struts connected to loops. Other similar helically coiled stent structures are known in the art, such as the stent design described in, for example, U.S. Pat. Nos. 8,382,821; 9,456,910; 9,155,639; 9,039,755 and 9,603,731 which are incorporated herein, in toto, by reference. These stent designs are configured as helical stents in which the coil is formed from a flat or tubular metal where the cells are formed from an undulating pattern of the helically wound coil.

In prior art stents, there typically is a tradeoff between longitudinal (or axial) flexibility and radial strength, as well as the ability to tightly compress or crimp the stent onto a catheter so that the stent can be more easily delivered through narrow tortuous vasculature (e.g., small side branches) and so that it does not move relative to the catheter or dislodge prematurely prior to controlled implantation in a vessel. Prior art stent designs also typically have a tradeoff between providing sufficient radial strength when the stent is expanded so that it can sufficiently support the vessel's lumen, and providing sufficient longitudinal flexibility so it can easily conform to the natural curvature of the vessel.

The crimped or compressed diameter of prior art stents is limited due to interference between adjacent struts, adjacent loops and/or a combination thereof. In addition, in self-expandable stents, interference between adjacent struts and/or loops may subject a portion of a strut to high stress/strain concentrations which may prevent the stent from fully expanding when deployed. For example, if a self-expanding stent is compressed beyond its elastic limit in an attempt to provide a smaller outside diameter, the stent will not return to its desired deployed expanded diameter due to permanent deformation.

Therefore, a continued need exists in the art for a stent having simultaneously sufficient radial strength, high degree of longitudinal flexibility and conformability to the vessel's natural curvature and movements, as well as a stent having a reduced compressed profile for enhanced delivery through small diameter or tortuous vessels (such as in side branches of the coronary vessel anatomy) and an enlarged expanded profile for deployment in large diameter vessels (such as in main branches of the coronary vessel anatomy), and while maintaining low stress/strain concentrations on portions of the stent. Thus, a need exists for a stent having an enlarged expanded diameter and a reduced compressed diameter in order to allow the stent to be used in any clinical situation compared to a conventional stent, while achieving optimal stress/strain distribution along the stent. Further, a need exists to limit the interference between adjacent struts and/or loops in the compressed profile in order to achieve a reduced compressed profile and a reduced stress/strain concentrations, as well as to minimize harmful interaction between adjacent struts. Minimizing harmful interactions between adjacent struts includes, for example, (a) reducing damage to stent coatings caused by contact between adjacent struts, (b) reducing the likelihood of damage to a balloon of a balloon catheter due to a material of the balloon being pinched between adjacent struts, (c) reducing stress imparted on the struts caused by the interaction between the adjacent struts, and/or (d) reducing the force required for crimping due to fewer strut-to-strut interactions.

SUMMARY OF THE INVENTION

The invention relates to a stent having an enlarged expanded diameter and/or a reduced compressed diameter, such that the stent has reduced outside diameter in its compressed state compared to conventional stents. The stent of the invention comprises a bent strut design in the crimped profile of the stent which reduces the compressed outside diameter compared to a compressed outside diameter of any given conventional stent. Any reduction of the compressed diameter is very significant clinically and allows for enhanced crimping.

The stent according to the invention comprises a continuous component having an undulating pattern of struts connected to loops which are helically wound. In one embodiment, at least one strut of the stent comprises one or more bends, curves or undulations in the strut design in at least the compressed configuration of the stent. For example, the bent strut design may include first and second bent, curved or angled sections facing in opposite convex and concave orientations. These opposing bends or angles join together at one or more locations along the strut. As the stent is compressed, a loop—oppositely aligned with a bent section (e.g., the first or second bent sections)—is moved a desired distance closer to the opposing bent section to form a nestled arrangement and achieve a desired smaller compressed diameter than in conventional stents. For example, the loop and the opposing bent section may be moved or compressed to substantially contact each other, where substantially contact is defined as a loop contacting or being in near contact with a bent section of the opposing strut. The nestled arrangement in the compressed configuration of the stent advantageously achieves a lower crimped profile than in conventional stents because the bend in the strut creates a space into which an opposing loop may nestle in the crimped orientation. The bent strut of the present invention may be utilized with any stent design having undulations.

One or more struts may include one or a plurality of bent sections, where the bent sections are distributed along the length of the stent as desired in the crimped delivery diameter. In one embodiment, the bent pattern may comprise first and second bent sections in opposite curvature extending from each end of the bent strut toward a mid-section of the bent strut such that the length of the bent strut comprises a concave curvature and a convex curvature. In one embodiment, all of the struts of the continuous component may be bent struts. In another embodiment, the continuous component may have a mixed strut design, such that some of the struts are bent struts and some of the struts are linear struts. In yet another embodiment, the continuous component does not comprise a bent strut. In this embodiment, first and second end rings, connected to the continuous component, may comprise bent struts.

Adjacent loops in the helical direction may be axially offset with respect to an axis perpendicular to the lengthwise direction to form a staggered pattern of alignment of adjacent loops such that a loop is positioned to align with an end of an adjacent strut in the helical direction. In one embodiment, the staggered pattern of alignment of adjacent loops is positioned such that, as the stent is compressed to the crimped delivery diameter, the loops adjacent to the first and second bent sections in the helical direction are positioned to align with and nestle in the first and second bent sections, respectively, to form a nestled arrangement. The nestled arrangement may be such that the loops adjacent to the first and second bent sections in the helical direction contact or are in near-contact with the first and second bent sections, respectively, when the stent is compressed to the crimped delivery diameter.

A strut may have a length different than the remaining struts. In one embodiment, a pair of struts comprise varying lengths, thereby contributing to the staggered pattern of alignment of adjacent loops, where the pair of struts comprise a long strut and a short strut, such that adjacent struts in the helical direction have the varying lengths.

A strut may have a varying width, e.g., a width near a mid-section of the strut is smaller than a width near ends of the strut, or vice versa. In this embodiment, a width of the loop may be greater than a width of any portion of the strut.

The stent comprises the continuous component having a tubular shape and extending from a first end to a second end along a lengthwise direction of the stent. The continuous component may comprise a plurality of windings having a crimped delivery diameter and an expanded implanted diameter. A winding may comprise any number of bands as desired for a particular application. For example, a winding may comprise a single band, or may comprise two, three, or four or more bands which may be interconnected as desired to form cells within the winding. It should be understood that features of the invention described herein, including the features contributing to the enlarged expanded diameter and/or the reduced compressed diameter, are applicable to a stent design having any number of bands in a winding. In one exemplary embodiment, each winding of the plurality of windings comprises two interconnected bands including a first band and a second band interconnected to one another to form cells there-between and oriented in a helical direction of the stent. The first and second bands may have an undulating pattern comprising struts and loops, where the loops are portions of the undulating pattern having a turn of about 180 degrees. Each end of a loop is coupled to an end of a strut to form a pair of struts.

The stent may further comprise a link interconnecting the two interconnected bands of each winding in the lengthwise direction. The two interconnected bands of each winding may be interconnected by a direct connection. In one embodiment, the link may be a straight connector and may extend in a gap between the two interconnected bands. The link and/or direct connection may connect first and second bands of the winding at loops on the first and second bands at a position where the gap between the interconnected bands is the shortest distance. The loops at which the first and second bands of a winding are connected may be referred to as attachment loops.

In another embodiment, the stent may further comprise a first end ring positioned at the first end and a second end ring positioned at the second end of the continuous component, where the first and second end rings may extend from the winding adjacent thereto. The first and second end rings may form approximately a right-angled cylinder at lengthwise ends of the stent. Each end ring may comprise one or more circumferential end bands interconnected in the lengthwise direction and may comprise the undulating pattern of loops coupled to pairs of struts. Similar to the windings of the continuous component, the circumferential end bands may be interconnected by a link and/or direct connection. In one embodiment, the transition between the windings of the continuous component and the first and second end rings may include at least one transition cell formed by the continuous component and one of the first and second end rings.

Further, similar to the continuous component, in one embodiment, the struts of the first and second end rings may have variable lengths to produce axially offset loops in the circumferential direction. Alternatively or in addition, the struts of the first and second end rings may have a variable width along the strut length, similar to that described with respect to the struts of the continuous component. Alternatively or in addition, the loops of the first and second end rings may have a width different than (e.g., larger or smaller) a width of any portion of the strut.

The first and second end rings may also similarly comprise at least one bent strut, where, as the stent is compressed to the crimped delivery diameter, at least one loop is positioned to align with and nestle in one of the first and second bent sections of the bent strut adjacent to the loop in the circumferential direction. In one embodiment, all of the struts of the first and second end rings may have bent struts. In another embodiment, the first and second end rings may have a mixed strut design, such that some of the struts are bent struts and some of the struts are linear struts. In yet another embodiment, the first and second end rings do not comprise a bent strut, but rather have linear struts.

The invention disclosed herein may relate to a coronary stent. However, the device according to the embodiments disclosed herein may be useful as a stent for non-coronary applications, for example a peripheral stent, a brain stent or other non-coronary applications. For coronary use, the stent may vary in length from 8-50 mm and have a deployed diameter of 1.5-6 mm. Further for coronary use, the stent may have a cell design with fewer interconnections (e.g., links or direct connections) and thus larger cells in order to provide a stent having cells sufficiently large for increased side branch access which is advantageous for use in the tortuous coronary vessels having multiple side branches. The cells of the stent may be the same or similar size along substantially the entire length of the stent or at least along the main body of the stent (excluding the ends) in order to provide similar side branch access throughout. The interval or number of interconnections may depend on the target stent diameter or the desired cell size.

DETAILED DESCRIPTION OF THE INVENTION

Figure 1:
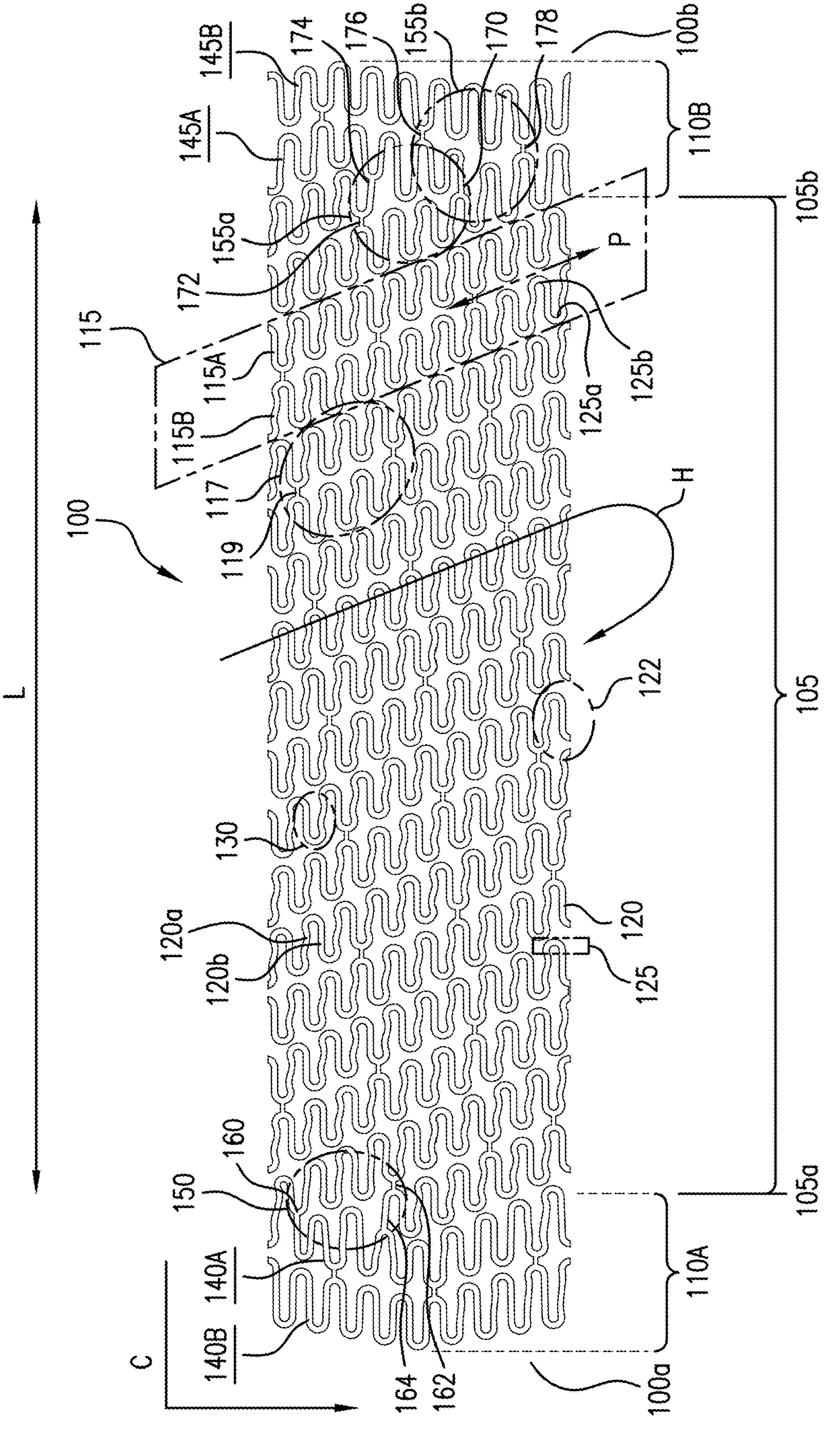
FIG. 1 illustrates a flat view of a stent in the as-cut configuration according to one embodiment of the invention.

This invention relates to stents, in particular, the stent of the invention improves on existing stents by providing an advantageously designed serpentine or undulating pattern of struts connected to loops which provides for a reduced crimped profile and/or an enlarged expanded profile, as well as an optimal stress/strain distribution along the stent. The stent may be longitudinally flexible and radially rigid, where longitudinal flexibility is defined as the ability of the stent to flex about an axis of the stent which extends in a lengthwise direction of the stent. The loops are defined as portions of the serpentine pattern having about a 180 degree turn (i.e., a U-turn), while the struts are portions of the serpentine pattern which have less than a 180 degree turn. Each end of the loop is connected to an end of a strut, such that each loop is connected to a pair of struts to form one undulation of the serpentine or undulating pattern.

The features of the invention, individually or in combination, advantageously provide for a stent having an increased expanded outside diameter in the expanded, deployed configuration and/or a reduced compressed outside diameter compared to conventional stents.

In particular, in one embodiment, the serpentine or undulating pattern of the stent is helically oriented in order to advantageously limit or avoid interference between adjacent loops in a crimped configuration of the stent. Due to the helical orientation, adjacent loops are advantageously axially offset with respect to an axis perpendicular to the lengthwise direction of the stent to form a staggered pattern. The staggered pattern of the helical arrangement may be a uniform stagger, such that adjacent loops in the helical direction do not have a scalloped edge or profile. Instead of alignment of adjacent loops in the helical direction, the staggered pattern advantageously allows for loops to be positioned in alignment with an adjacent strut in the helical direction of the stent, which thereby avoids some of the interference between adjacent loops in the crimped configuration. The loops may be positioned in alignment with an end of the adjacent strut. Because loops have a large turn radius, the crimped diameter of the loops is still limited and the loops are the largest part of the stent in the crimped configuration of the stent.

The loops of the undulating pattern may be connected to two struts of varying lengths, such that the undulating pattern of the stent comprises alternating long and short struts. This arrangement of varying the strut lengths also advantageously limits or avoids the interference between adjacent loops in the crimped configuration of the stent. An alternating pattern of long and short struts contributes to the reduced crimped profile of the stent by advantageously generating a staggered or offset pattern of adjacent loops with respect to a transverse axis, namely, an axis perpendicular to the lengthwise direction of the stent. The staggered pattern of adjacent loops advantageously avoids the interference between adjacent loops in the crimped configuration.

In addition to reducing the crimped profile, the arrangement of varying the strut lengths further provides the advantage of allowing for an enlarged expanded profile. Longer strut lengths are capable of expanding to a larger diameter when deployed than are shorter struts. By providing a stent having an alternating arrangement of long and short struts, where each loop is connected to one long strut and one short strut, the stent of the invention may advantageously expand to an enlarged expanded profile (due to the long strut) and compress to a reduced crimped profile (due, at least in part, to the short strut contributing to the staggered pattern). Further, the alternating arrangement of long and short struts, also advantageously contributes or enhances the flexibility of the stent, as well as the scaffolding and vessel wall coverage.

The arrangement of varying strut lengths may depend on the particular application of the stent and may be varied in a random or in a repeating periodic pattern. For example, one, some or all pairs of struts may comprise two struts of varied lengths (e.g., one long strut and one short strut). Where one or some of the pairs of struts comprise struts of varied lengths, the remaining pairs of struts may comprise two struts of the same length. Further, for example, the lengths of the struts may vary between different pairs of struts, such that, for example, a long strut of one pair may have a different length than a long strut of another pair, and/or a short strut of one pair may have a different length than a short strut of another pair. The strut lengths in the end rings may be varied in a same or different pattern than the strut lengths of the continuous component. In one embodiment, the struts of the end rings may not have variable lengths (i.e., may have the same lengths), while at least one strut of the continuous component may have a varied length. Alternatively, at least one strut of the end rings may have a variable length, while the strut of the continuous component may have the same lengths.

A strut of the present stent may have one or more bent sections, e.g., first and second bent sections in opposite curvature extending, from each end of the strut, toward an intersection point of the strut (e.g., at a mid-section of the strut). In one embodiment, the struts are bent, curved or arched, such that the struts are not straight or linear from one end of the strut to the other end, particularly, in the crimped configuration. In a pair of struts connected to a loop, the curvature of the bent section of the strut nearest the loop may bend inward (e.g., concave) toward the opposing strut of the pair, while the curvature of the bent section of the strut furthest from the loop may bend outward (e.g., convex) away from the opposing strut of the pair, such that the strut has a concave bent section and a convex bent section. The bent design of the strut may be referred to as a bent structure where the end of the strut connected to an end of a loop bends inward toward a center of the loop and then outward away from the center of the loop. This bent pattern of the struts exists and is maintained in the crimped, unexpanded, configuration as well as in the deployed, expanded, configuration of the stent, and during the configuration change, such that the bent sections do not substantially straighten. The bent pattern in a strut creates a space or a hollow section for an adjacent loop to fit therein in a nestled or nested arrangement as the stent is compressed, which in turn advantageously allows tighter packing or compressing of the stent in the crimped configuration. The bent strut pattern allows for the loops to nest into the bent section (e.g., the concave portion) of struts which are adjacent or opposite the loops in the helical direction when the stent is compressed into the crimped profile, thereby advantageously providing a reduced crimped profile. A stent of the present invention having at least one bent strut in the crimped configuration will advantageously have a compressed diameter smaller than a compressed diameter of a conventional stent having a strut which is substantially straight or substantially straightens during or when compressed because a straight or substantially straight strut does not allow for the advantageous nested arrangement of the present invention.

The number and/or arrangement of the bent struts may depend on the particular application of the stent, where the number of bent struts is inversely proportional to the crimped, delivery, diameter of the stent. For example, a stent for coronary use may have more bent struts than a stent for peripheral use because the coronary vessel anatomy is narrower than peripheral vessel anatomy and therefore would require a smaller crimped profile than the crimped profile for use in the peripheral vessel anatomy. A stent according of the invention, in the compressed and/or expanded configuration(s), may also have any combination of non-bent or straight/linear struts, bent struts for the long and/or the short struts, struts having different lengths, and struts having same or similar lengths some of which may be straight/linear struts while other struts are bent. Further, a stent may have such different strut lengths in a random pattern or repeating uniform pattern.

In the compressed configuration of the stent, at least some struts are bent while others may not be bent (i.e., are straight) in a uniform or random pattern. For example, alternating struts are bent, where, for example, only the long struts are bent. In another embodiment, the struts near the ends of the stent may not be bent while the remaining struts may be bent, or vice versa. In an embodiment where opposing struts of a pair of struts (i.e., two consecutive struts) each have one or more bends, the bends of the opposing struts may be out-of-phase (e.g., mirror image), but need not be in other embodiments. In another embodiment, substantially all struts of the stent include one or more bent sections, where no (or substantially no) struts are straight, in at least the compressed configuration of the stent. "Substantially all struts" may be defined as about 75% or more of the struts of the stent.

The bent strut design, in combination with the staggered pattern of adjacent loops in the helical direction, allows the loops to be positioned in alignment with an end of an adjacent strut in the helical direction such that, as the stent is compressed to the crimped profile, the loops are positioned to advantageously align with and nestle in the (e.g., concave) bent section of the adjacent strut (in the helical direction) which bends inward toward the adjacent loop. Because the loop (which is the largest part of the stent pattern due to its turn radius) advantageously nestles in the (e.g., concave) bent section of an adjacent strut, the crimped profile of the stent may be further reduced, where interference between adjacent loops are avoided and interference between a loop and an adjacent strut is reduced. Thus, while the staggered pattern of adjacent loops reduces the crimped profile by minimizing the interference produced by adjacent loops, the bent strut design further reduces the crimped profile by additionally minimizing interference between a loop and an adjacent strut. Interference between a loop and an adjacent strut is reduced because the bent section of the strut at least partially envelopes the adjacent loop, for example, enveloping one end of the loop to about a mid-section of the loop. The bent strut design allows the bent section of the strut (opposite an adjacent loop in the helical direction) to have a complementary shape to the adjacent loop such that there is a complementary or lock-and-key fit between a loop and the opposing bent section of the adjacent strut. Thus, the crimped profile of the present invention is further reduced because the bent section advantageously conforms to and allows nestling of the adjacent loop. As such, the bent sections of the struts advantageously maintain the bent strut pattern (and are not straight or straighten) in the crimped configuration of the stent.

Optimal stress/strain distribution along the stent may be further advantageously achieved by redistributing the stress/strain forces imparted on the stent to prevent permanent deformation of the stent, and enable the stent to fully expand or fully compress. The stress/strain imparted on the stent may be advantageously redistributed by varying the relative strength or flexibility of different portions of the stent, such as by redistributing the stress/strain forces away from the loops. For example, the amount of material used to form different portions of the stent can be varied to change the portions' relative strength or flexibility. This variation in strength or flexibility of stent portions can be accomplished by increasing the thickness or width of the loop portions to increase the strength of these portions relative to the strut portions, thereby redistributing stress/strain forces away from the loop portions. Alternatively or in addition, the strut width is also gradually decreased from both ends towards the strut's mid-section to further redistribute stress/strain forces away from the loop portions and toward the mid-section of the strut portion of the stent.

In one embodiment, the stent, may comprise a polymer material. The polymer material may be electrospun onto the stent. The polymer material may interconnect at least two of the plurality of windings of the stent. The polymer material may be a biodegradable polymer, or may be another polymer. In one embodiment, the polymer material may further comprise a drug embedded therein.

FIG. 1 illustrates a stent 100 in the as-cut configuration according to an embodiment of the invention which, for illustration purposes only, is shown in a longitudinally opened and flattened view. In use, the stent 100 has a tubular shape and may be manufactured from an extruded tube, or a flat sheet which is rolled into the tubular shape. The desired stent design or pattern may be laser cut onto the extruded tube, or may be laser cut or chemically etched onto the flat sheet which is then rolled. The stent 100 of FIG. 1 is shown in the as-cut configuration, which is a neutral profile of the stent 100 when the stent 100 has been formed (i.e., manufactured), but not yet crimped to the delivery diameter and not yet expanded to the implanted deployed diameter.

The stent 100 is a tubular structure having a continuous component 105 extending from a first end 105*a* to a second end 105*b* along a lengthwise direction L of the stent 100. The continuous component 105 is arranged to have a helical orientation along a helical direction H of the stent 100. In one embodiment, as shown in FIG. 1, the continuous tubular structure includes a first end ring 110A and a second end ring 110B positioned to extend from the first end 105*a* and the second end 105*b*, respectively. The first and second end rings 110A-B extend in a circumferential direction C around a circumference of the stent 100 such that the first and second end rings 110A-B, at lengthwise ends 100*a-b* of the stent 100, are oriented approximately at a right or 90° angle to the lengthwise direction L to form a right-angled cylinder. Approximately at a right angle with respect to the first and second end rings 110A-B is defined as oriented at any angle closer to 90° than the helical orientation of the continuous component 105. In another embodiment (not shown), the stent 100 is the continuous component 105 without the first and second end rings 110A-B, such that lengthwise ends 100*a-b* of the stent 100 are the first and second ends 105*a-b* and do not form a right-angled cylinder relative to the lengthwise direction of the stent.

The continuous component 105 includes a plurality of windings 115. The windings 115 are continuously oriented in the helical direction H between the first and second ends 105*a-b*, such that the windings 115 are oriented at an oblique angle to the lengthwise direction L of the stent 100. Each winding 115 may include one or more bands. In the exemplary embodiment shown in FIG. 1, each winding 115 includes a first band 115A and a second band 115B which are interconnected to one another, thereby forming two interconnected bands 115A-B. The first band 115A and the second band 115B are interconnected to one another to form cells 117 there-between and are oriented in the helical direction H of the stent 100, such that the cells 117 form a helix of cells between the first end 105*a* and the second end 105*b*. The area enclosed by the cells 117 are open spaces or gaps between the interconnected bands 115A-B.

The first and second bands 115A-B each has a serpentine or undulating pattern and extend generally parallel to each other in the helical direction H. The undulations of the first and second bands 115A-B comprise struts 120 connected to one another by a pattern of loops 125, referred to as peaks 125*a* and valleys 125*b*.

The loops 125 are portions of the undulating pattern having a turn of about 180 degrees (i.e., a U-turn), while the struts 120 do not. One or more of the struts 120 may have one or more bends (e.g., one or more bent sections) having a turn of less than 180 degrees. Some of the struts 120 may have no bends (i.e., may be straight or linear members). Each end of a loop 125 is coupled to an end of a strut 120, thereby forming a pair of struts 122 connected to a loop 125. The pair of struts 122 are two struts connected to a common loop and which are adjacent to each other in the helical direction H within a winding 115.

The number and/or location of the struts 120 having a bent strut design may vary depending on a particular application. A stent 100 having more struts 120 which are bent results in a greater reduced crimped profile because bent struts of the invention allow for tighter packing in the helical direction H between adjacent loops 125 and struts 120 (at, e.g., the first and second bent sections 135*a-b* shown in FIGS. 2-3) and allow for avoidance of interference (or contact) between adjacent loops 125. For example, a stent 100 for implantation in coronary vessels may have more struts 120 with the bent strut design than a stent 100 for implantation in peripheral vessels, where coronary vessel anatomy generally contains narrower and more tortuous vessels than the peripheral vessel anatomy. In an embodiment having a mixed bent/linear strut design, the struts 120 which are not bent (i.e., linear) may be at or near the lengthwise ends 100*a-b* of the stent 100, such as, for example, in the first and second end rings 110A-B and/or in the windings 115 at the first and second ends 105*a-b* of the continuous component 105. Alternatively or in addition, the struts 120 which are not bent (i.e., linear) may be randomly or uniformly located throughout the stent 100.

The loops 125 form the serpentine pattern such that the peaks 125*a* and valleys 125*b* are arranged in an alternating pattern in the helical direction H of each of the first and second bands 115A-B. The peaks 125*a* are the loops 125 which curve toward the opposing interconnected band 115A-B of a winding 115 and thus are the outer loops 125*a* of the cell 117. The valleys 125*b* are the loops 125 which curve away from the opposing interconnected band 115A-B of a winding 115 and thus are the inner loops 125*b* of the cell 117. The valleys 125*b* are closer, along the lengthwise direction L, to the center of a cell 117 enclosed by the interconnected bands 115A-B than are the peaks 125*a*. The center of the cell 117 are points along a point axis P extending between two points of interconnection which interconnect the first and second bands 115A-B to define a cell 117. The number, type and/or location of interconnections in each winding 115 of the stent may be at regular or uniform intervals (e.g., every third pair of helically adjacent valleys 125*b* shown in FIG. 1) or may be at random intervals, and may depend on a particular application (e.g., coronary or peripheral vessel applications). Some or all of the interconnections may extend substantially lengthwise along the lengthwise direction L of the stent 100, but may extend or be oriented along other directions (e.g., circumferentially and/or helically).

As shown in FIG. 1, the two interconnected bands 115A-B in a winding 115 may be substantially out-of-phase with each other such that, along the lengthwise direction L, peaks 125*a* of the first and second bands 115A-B are substantially aligned with or face each other, and valleys 125*b* of the first and second bands 115A-B are substantially aligned with or face each other. In this out-of-phase embodiment, a distance (i.e., open space or gap) spanning a length of the cell 117 (along the lengthwise direction L) between aligned valleys 125*b* of the first and second bands 115A-B in a winding 115 is smaller than a distance spanning the length of the cell 117 between aligned peaks 125*a* of the first and second bands 115A-B in the winding 115. In another embodiment (not shown), the two interconnected bands 115A-B in a winding 115 may be substantially in-phase with each other such that, along the lengthwise direction L, peaks 125*a* of the first band 115A may be substantially aligned with or face valleys 125*b* of the second bands 115B. In another embodiment, the stent 100 may have mixed phase interconnected bands 115A-B in a winding 115, such that some or at least one interconnected band 115A-B in a winding 115 may be substantially out-of-phase with each other, while the remaining interconnected bands 115A-B in remaining windings 115 may be substantially in-phase with each other.

As shown in FIG. 1, a first band 115A in a winding 115 and a second band 115B in an adjacent winding 115 may be substantially in-phase with each other such that, along the lengthwise direction L, peaks 125*a* of the first band 115A may be substantially aligned with or face valleys 125*b* of the second bands 115B of the adjacent winding 115. In another embodiment (not shown), the first band 115A in the winding 115 and the second band 115B in an adjacent winding 115 may be substantially out-of-phase with each other such that, along the lengthwise direction L, peaks 125*a* of the first band 115A are substantially aligned with or face peaks 125*a* of the second band 115B of the adjacent winding 115, and valleys 125*b* of the first band 115A are substantially aligned with or face valleys 125*b* of the second band 115B of the adjacent winding 115. In yet another embodiment, the stent 100 may have mixed phase adjacent windings 115, such that some or at least one first band 115A in a winding 115 and a second band 115B in an adjacent winding 115 may be substantially in-phase with each other, while the adjacent first and second bands 115A-B in the remaining adjacent windings 115 may be substantially out-of-phase with each other.

The loops 125 are axially offset with respect to a perpendicular axis to the lengthwise direction L. In the embodiment shown in FIG. 1, an apex (outer tip) of a loop 125 is aligned with an end of an adjacent or opposing strut 120 at the end connected to the adjacent loop 125. The staggered pattern of alignment A of adjacent loops in the helical direction H is identified in FIG. 2, where the apex 125*c* of a loop 125 is aligned with an end 120*c* of an adjacent strut 120 in the helical direction H. Other staggered patterns of alignment may be incorporated into the stent 100 of the present invention, where the plurality of windings 115 of the stent 100 may have a consistent staggered pattern of alignment, or may have varied staggered patterns of alignment, for example, in different windings 115 and/or within the same winding 115.

In FIG. 1, the pair of struts 122 comprise two struts 120 having different lengths connected to a common loop 125. For example, the pair of struts 122 comprise a one long strut 120*a* and one short strut 120*b*, where a length of the long strut 120*a* is longer than a length of the short strut 120*b*. In FIG. 1, the lengths of the long strut 120*a* and the short strut 120*b* are sized such that adjacent loops 125 in the helical direction H are axially offset with respect to a perpendicular axis to the lengthwise direction L of the stent 100 to form the staggered pattern of alignment A of adjacent loops, where a loop 125 (e.g., at its apex 125*c*) is positioned to align with an end 120*c* of an adjacent strut 120.

The stent 100 comprises at least one strut 120 or one pair of struts 122 having a length different than the remaining struts 120 or pairs of struts 122 of the stent 100. Alternatively, in another embodiment (not shown), the stent of the invention may comprise struts of all the same length. In the embodiment shown in FIG. 1, the long and short struts 120*a-b* are arranged in an alternating arrangement about the helical direction H. The strut lengths may be similarly varied in the first and second end rings 110A-B. In the embodiment shown in FIG. 1, at least one strut 120 of the first and second end rings 110A-B has a length different than the remaining struts 120 of the first and second end rings 110A-B, and at least one strut 120 of the continuous component 105 has a length different than the remaining struts 120 in the continuous component 105.

The stent 100 of FIG. 1 includes at least one strut 120 having a bent strut design facilitating the reduced compressed profile of the stent 100. The bent strut design or pattern comprises at least one strut having one or a plurality of bends along the strut length. Where the strut length includes a plurality of bends, at least one strut 120 includes at least two bends which face opposite each other such that the pair of struts 122 connected by a loop 125 form a bent pattern, structure or shape 130, as shown in FIG. 1. In the crimped configuration of the stent 100, the bent strut design of at least one strut 120 having at least two opposing bends allows for adjacent loops 125 (e.g., bottom and top loops 125*d-e* of FIG. 2) in the helical direction H to nestle in the two opposing bends, respectively, thereby providing a reduced compressed diameter. Alternatively or in addition, at least one strut 120 of the stent 100 may form the bent shape 130 along a length of the strut 120, such that, in the crimped configuration of the stent 100, at least one adjacent loop 125 (e.g., a top or a bottom loop 125) in the helical direction H nestles in the opposing bend of the strut 120, thereby providing a reduced compressed diameter. In an embodiment (not shown), at least one strut 120 comprises a bent strut design where the strut 120 has one curve in a first section along the strut 120 length, while the remaining length of the strut 120 is linear or straight (i.e., absent a curve), such that an adjacent loop 125 (e.g., a top or bottom loop 125) in the helical direction H may nestle in the bent first section of the strut 120, in the crimped configuration of the stent 100. The one or more bends in at least one strut 120 of the stent 100 (in any and all embodiments) are maintained in the crimped profile of the stent 100, such that when the stent is compressed or during compression, the one or more bends do not substantially straighten, and thereby providing the nestled arrangement and reduced crimped profile of the stent 100.

Figure 2:
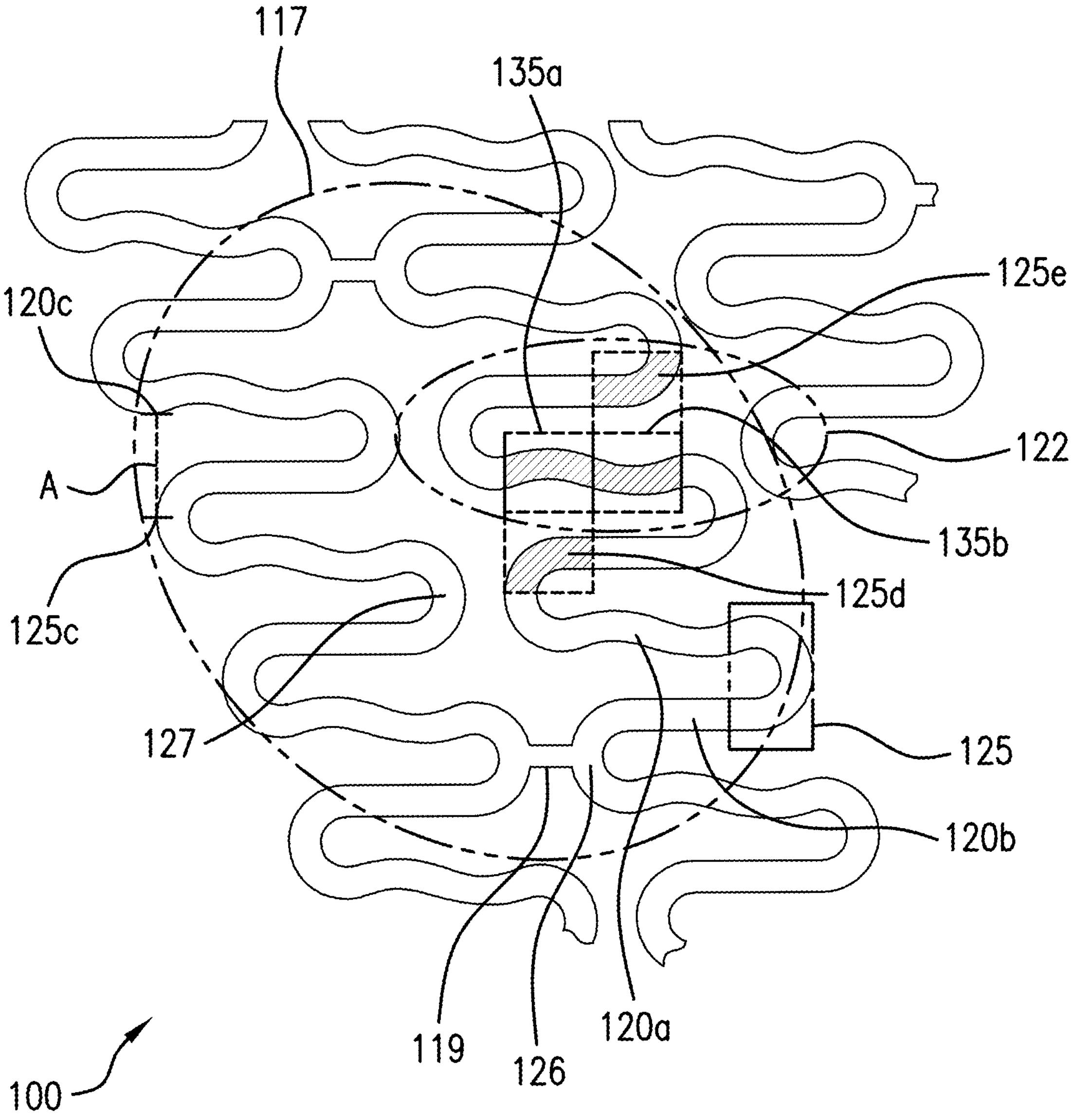
FIG. 2 is an enlarged view of an enclosed cell of the continuous structure of the stent of FIG. 1.

FIG. 2 illustrates an enlarged view of an enclosed cell 117 of the continuous structure 105 of the stent 100 of FIG. 1, where the bent strut design is more clearly identifiable. The bent strut design of at least one strut 120 includes a first bent section 135*a* and a second bent section 135*b* extending in an opposite direction from each end 120*c* of the strut 120 toward a mid-section of the strut 120, where each end 120*c* is the portion of the strut 120 contiguous with a loop 125. One of the bent sections 135*a-b* is preferably convex while the other bent section 135*a-b* is concave. For example, in a pair of struts 122 having at least one strut 120 with the bent strut design, the first bent section 135*a* of the strut 120 extends from the end of the loop 125 coupled to the pair of struts 122 and curves inwards (e.g., concave) toward an opposing strut 120 of the pair 122 to form the bent structure 130. The second bent section 135*b* of the strut 120 extends from the mid-section of the strut 120 to an end of an adjacent loop 125 in a substantially the lengthwise direction L, where the second bent section 135*b* bends outwards away (e.g., convex) from the opposing strut 120 of the pair 122 to form the bent structure 130. The bent strut design (e.g., the first and second bent sections 135*a-b*) creates a space, hollow or area/volume for an adjacent loop 125 (e.g., 125*d-e*) in the helical direction H to fit in the space created (i.e., nestle in the bent sections 135*a-b*) when the stent 100 is compressed or is in the crimped, delivery configuration. For example, the nestled arrangement is such that, as the stent is compressed, the first bent section 135*a* and the adjacent loop 125*d* below the first bent section 135*a* (in the helical direction H) move toward each other so that the below adjacent loop 125*d* nestles into the first bent section 135*a* in the crimped, delivery configuration. Similarly, as the stent is compressed, the second bent section 135*b* and the adjacent loop 125*e* above the second bent section 135*b* (in the helical direction H) moves toward each other so that, in the crimped delivery configuration, the above adjacent loop 125*e* nestles into the second bent section 135*b*. In the as-cut configuration of the stent 100, shown in FIG. 2, the first and second bent section 135*a-b* are aligned (along a perpendicular axis to the lengthwise direction L) with, but not nestled with, adjacent bottom and top loops 125*d-e*, respectively. Similarly, in the expanded, implanted or deployed, configuration of the stent 100, the first and second bent section 135*a-b* may be aligned (along a perpendicular axis to the lengthwise direction L) with, but not nestled with, adjacent bottom and top loops 125*d-e*, respectively.

The area of the first and second bent sections 135*a-b* which are aligned and configured to nestle with respective bottom and top adjacent loops 125*d-e* in the crimped profile of the stent 100 are illustrated in FIG. 2 by the cross-hatching. As illustrated in FIG. 2, the first bent section 135*a*, at an end of the strut 120, is aligned with the apex 125*c* of the below adjacent loop 125*d* in the helical direction H, while the first bent section 135*a*, near the mid-section of the strut 120, is aligned with an end of the below adjacent loop 125*d*, such that the first bent section 135*a* aligns with an adjacent (e.g., bottom) loop 125*d*. As such, adjacent loops 125 in the helical direction H are axially offset, i.e., staggered, with respect to a perpendicular axis to the lengthwise direction L. The staggered pattern of alignment A of adjacent loops in the helical direction H are staggered such that overlap between adjacent loops 125 is avoided or limited when the stent 100 is compressed to the crimped profile, thereby allowing for a reduced compressed diameter. Further, the staggered pattern of alignment A of adjacent loops is such that an adjacent loop 125 is positioned to align (along a perpendicular axis to the lengthwise direction L) with the respective, opposing, bent section 135*a-b* of the adjacent strut 120 where, as the stent 100 is compressed to the crimped profile, the loop 125 nestles in the respective, opposing, bent sections 135*a-b*, thereby further reducing the compressed diameter. In one embodiment, the nestling arrangement may be such that at least one loop 125 has a substantially complementary fit with an opposing bent section 135*a-b* in the helical direction H. The nestling arrangement may be such that at least one loop 125 is nestled to contact (or be in near-contact with) the opposing bent sections 135*a-b* when the stent is in the crimped configuration.

The first and second bent section 135*a-b* do not substantially straighten during compression or when the stent 100 is in the compressed configuration such that the first and second bent sections 135*a-b* maintain their respective bent patterns and allow for a reduced crimped profile of the stent 100. In any and all embodiments of the present invention, the first and/or second bent sections 135*a-b* of at least one strut 120 must be bent (e.g., either maintain or become more bent), as the stent 100 is compressed or when the stent 100 is in the compressed configuration, so that at least one adjacent loop 125 in the helical direction H is configured to nestle in the opposing or respective first and/or second bent section 135*a-b*, thereby reducing the compressed diameter of the stent 100. In one embodiment, the first and second bent sections 135*a-b* are bent (i.e., do not straighten) in the crimped, as-cut, and expanded diameters of the stent 100. In another embodiment, in order to provide for an enlarged expanded diameter, the first and/or second bent sections 135*a-b* may substantially straighten in the expanded, deployed profile of the stent 100 such that the first and/or second bent sections 135*a-b* become more straight compared to the more bent crimped or as-cut profiles or may become entirely straight. The struts 120 may substantially straighten in the expanded profile and/or may become more bent in the crimped profile because the struts 120 are flexible.

The amount of curvature of the first and second bent sections 135*a-b* may depend on a particular application, where a higher bend in the first and second bent sections 135*a-b* may result in a greater reduced crimped profile, and may therefore be preferable in coronary applications in contrast to peripheral applications. The amount of curvature may be defined as the curvature angle of each of the first and second bent sections 135*a-b*, respectively. The curvature angle is created by the bend of the strut 120 at the first and second bent sections 135*a-b* and provides a gap, space or hollow such that the adjacent loop may nestle therein in the crimped configuration of the stent 100. The curvature angle provides a maximum height 137 (FIG. 3) of the gap, space or hollow created by the one or more bends of the strut 120. The curvature angle is less than 90 degrees but greater than zero degrees, and may be greater than 35 degrees. The amount of curvature of the first and second bent sections 135*a-b* of a strut 120 may be the same or different, and the amount of curvature in different struts 120 may be the same or different. In one embodiment, the height 137 (FIG. 3) of the curvature (i.e., the maximum height 137 of the gap or space created by the bend of the first and/or second bent sections 135*a-b*) may be greater than 0 microns but less than about 150 microns, and may preferably be at least 30 microns. Alternatively or in addition, the height 137 of the curvature may be substantially the same as or equal to the width of the loop 125 (for example, at the width of the loop 125 at the portion which is configured to nestle within the space created by the bend of the bent sections 135*a-b*). Alternatively, the height 137 of the curvature may be about half the width 139 (FIG. 3) of the loop 125.

Similarly, the number and/or location of the struts 120 having a bent strut design may vary depending on a particular application. The stent 100 includes at least one strut 100 having the bent strut design of at least one of the first and second bent sections 135*a-b*. In the embodiment shown in FIGS. 1 and 2, for example, a mixed bent/linear strut design is illustrated in an alternating pattern such that each pair of struts 122 includes the long strut 120*a* having the first and second bent sections 135*a-b* in opposite orientation, and the short strut 120*b* which is linear. In the embodiment shown in FIGS. 1-2, the continuous component 105 includes the alternating pattern of bent long struts 120*a* and linear short struts 120*b*, while the struts 120 of the end rings 110A-B are linear and not bent. However, in other embodiments and as required for a particular application, the end rings 110A-B may include at least one strut 120 having a bent strut design. Further, in other embodiments with the alternating pattern, the short strut 120*b* may comprise the bent strut design and the long strut 120*a* may be linear, or both struts 120 of the pair 122 (e.g., the long and short struts 120*a-b*) may comprise the bent strut design.

In the embodiment shown in FIGS. 1-2, the first and second bands 115A-B are connected to each other to form the cells 117 by at least one link 119. The links 119 are connectors or cross-struts which extend in the lengthwise direction L of the stent 100 and/or may extend in a diagonal direction (not shown) to form the two interconnected bands 115A-B and enclose a cell 117. The links 119 extend in a gap between the first and second bands 115A-B, thereby closing or forming the cells 117. The links 119 may be flexible connectors, thereby enabling the stent 100 to conform to the curvature of a vessel anatomy. In the embodiment shown in FIG. 1, the links 119 are straight or linear connectors absent a bend. Alternatively, in another embodiment (not shown), the links 119 may have one or more loops or bends, or some links 119 may be linear connectors while other links 119 in the stent 100 may have loops or bends. Alternatively to links 119, the first and second bands 115A-B may be connected directly to each other to form the cells 117 absent links 119. In another embodiment, the stent 100 may include a combination of links 119 and direct connections for interconnecting the first and second bands 115A-B in a winding 115. Other interconnections and direct connections may be achieved and are within the scope of the present invention, such as, for example by weld, adhesive, metal connectors, a polymer material, or any form of physical joining or other securement, interlock or connection means. The loops 125 at which the interconnections are positioned may be referred to as attachment loops 126 and the loops 125 at which no interconnection is positioned may be referred to as free loops 127, as shown in FIG. 2.

The number, type, and/or location (e.g., interval or placement) of interconnections (e.g., links 119 and/or direct connections) may depend on a particular application (e.g., coronary or peripheral vessel applications), where the interconnections determine the size and shape of the cell 117. In the exemplary embodiment shown in FIGS. 1-2, the first and second bands 115A-B in a winding 115 are connected by links 119 at every sixth loop 125 (or every third valley 125*b*), for example. Accordingly, in the exemplary embodiment shown in FIGS. 1-2, each cell 117 is enclosed by two links 119 (between attachment loops 126), twelve struts 120, and ten free loops 127. Further, for example, as shown in FIG. 2, the attachment loops 126 are valleys 125*b*, such that the links 119 are positioned to connect the apex of a valley 125*b* of the first band 115A and the apex of a valley 125*b* of the second band 115B which are aligned along the lengthwise direction L. As such, in this embodiment, the links 119 are arranged to connect the first and second bands 115A-B at locations at which the gap or distance there-between is the smallest, which thus results in a shorter link 119 (compared to a link that may span the largest distance between the two interconnected bands 115A-B). In alternative embodiments, the number, interval and/or location of the interconnections (i.e., links 119 or direct connections) may differ from that illustrated in FIGS. 1-2.

In some embodiments, the links 119 may each have the same width relative to each other and/or to the first and second bands 115A-B or a portion thereof. Alternatively, the links 119 may have a different width, for example, a smaller width than the first and second bands 115A-B (or any portion thereof), or a different width from each other, as appropriate for a particular use. Links 119 having a narrower width provide for greater flexibility to the stent than links 119 having wider widths, while links 119 with wider widths provide greater structural integrity and rigidity to the stent. The links 119 may have a uniform thickness along the link length or a variable thickness. Further, in some embodiments the plurality of links 119 have the same lengths or varying lengths at uniform or random intervals. In one embodiment, for a coronary stent, links 119 may vary in length from 0.05 mm to 0.15 mm and may vary in width from 0.03 mm to 0.07 mm. In another embodiment, for a peripheral stent, links 119 may vary in length from 0.5 mm to 1.0 mm and may vary in width from 0.05 mm to 0.1 mm. The lengths and widths of the links 119 may depend on the stent application (e.g., coronary or peripheral), type of deployment (e.g., balloon expandable or self-expandable) and/or stent target diameter.

Similarly, the lengths and widths of the struts 120 may depend on the stent application (e.g., coronary or peripheral), type of deployment (e.g., balloon expandable or self-expandable) and/or stent target diameter. All or some of the struts 120 may have a same width and/or length relative to each other, or a different width and/or length from each other. In one embodiment, for a coronary stent, struts 120 may vary in length from 0.5 mm to 1.5 mm and may vary in width from 0.04 mm to 0.1 mm. In another embodiment, for a peripheral stent, struts 120 may vary in length from 1.3 mm to 2.5 mm and may vary in width from 0.08 mm to 0.14 mm. Further, all or some of the struts 120 may have a single width from one end of the strut 120 to the other end, or all or some of the struts 120 may have more than one width along the length of the strut 120 from one end to the other end. The struts 120 (at any portion along the strut length) may have a same or different width than the loop 125.

Figure 3:
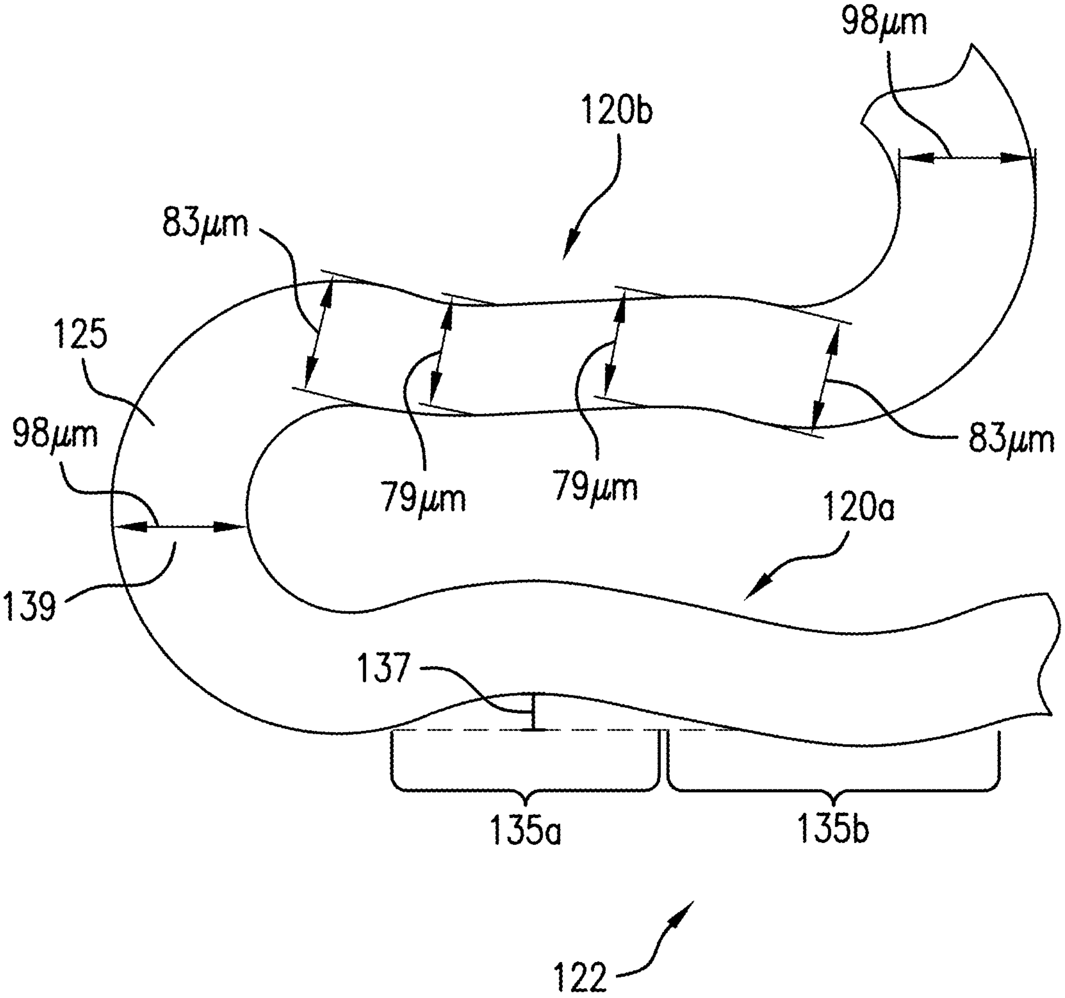
FIG. 3 is an enlarged view of a pair of struts connected to a loop of a stent in the as-cut configuration according to another embodiment of the invention.
Figure 4:
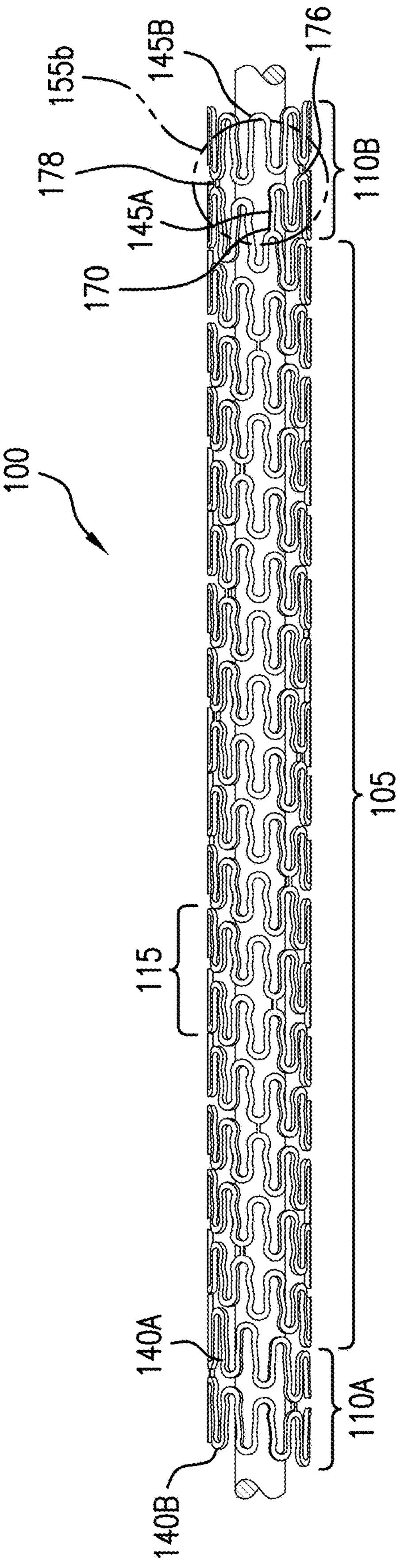
FIG. 4 illustrates a 3-dimensional model of the stent, according to the embodiment of FIG. 3, from a first perspective and in the as-cut configuration.
Figure 5:
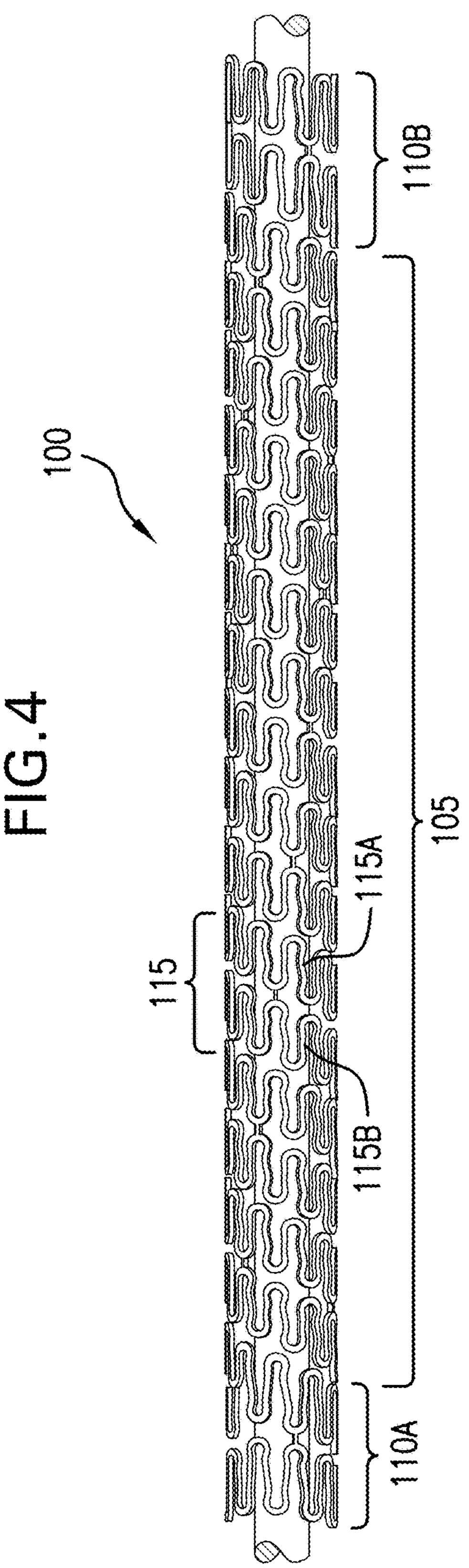
FIG. 5 illustrates a 3-dimensional model of the stent according to FIG. 4 from a second perspective and in the as-cut configuration.
Figure 6:
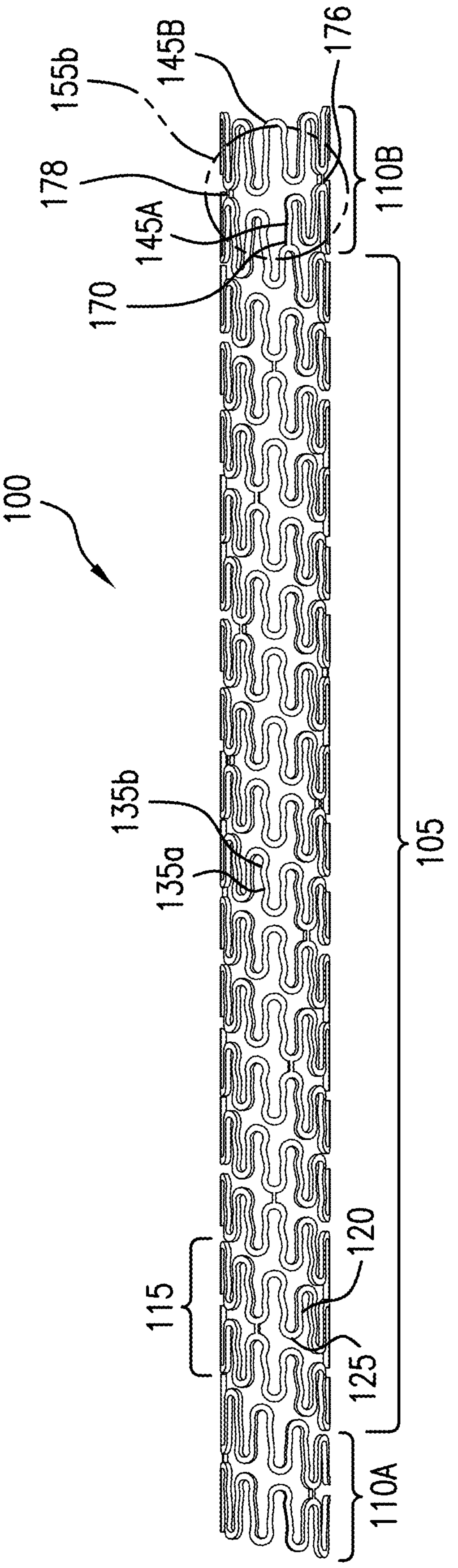
FIG. 6 illustrates a 3-dimensional model of the stent according to FIG. 4 from the first perspective and in the as-cut configuration.
Figure 7:
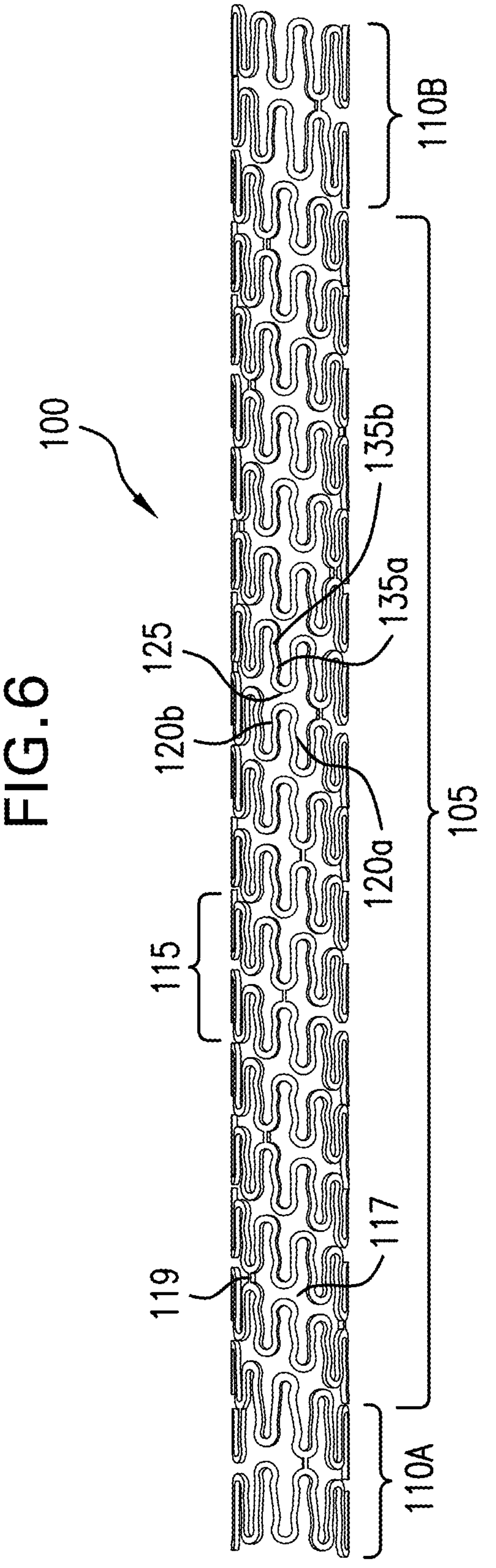
FIG. 7 illustrates a 3-dimensional model of the stent according to FIG. 5 from the second perspective and in the as-cut configuration.
Figure 8:
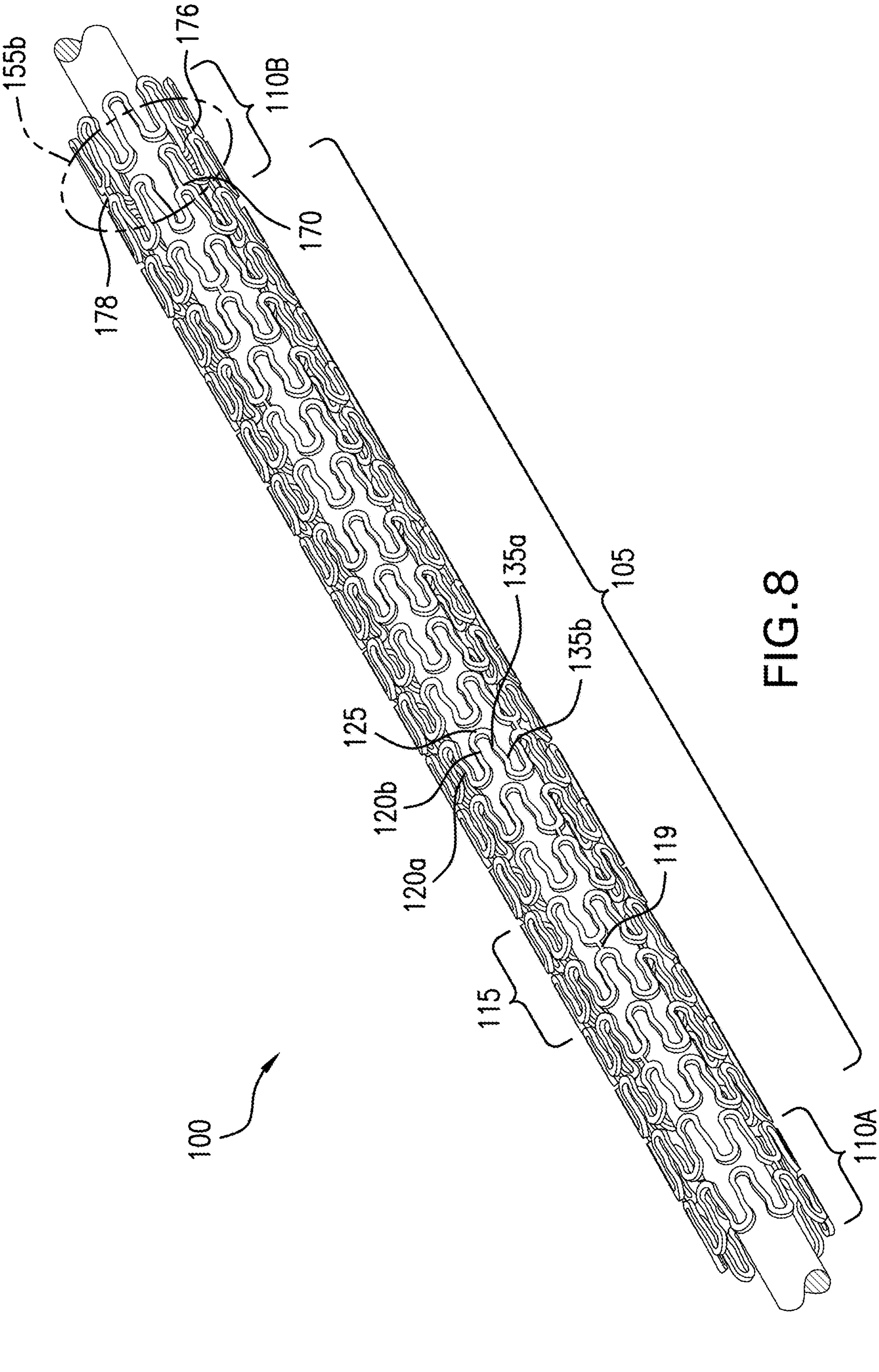
FIG. 8 illustrates a 3-dimensional model of the stent according to FIG. 4 from the third perspective and in the as-cut configuration.
Figure 9:
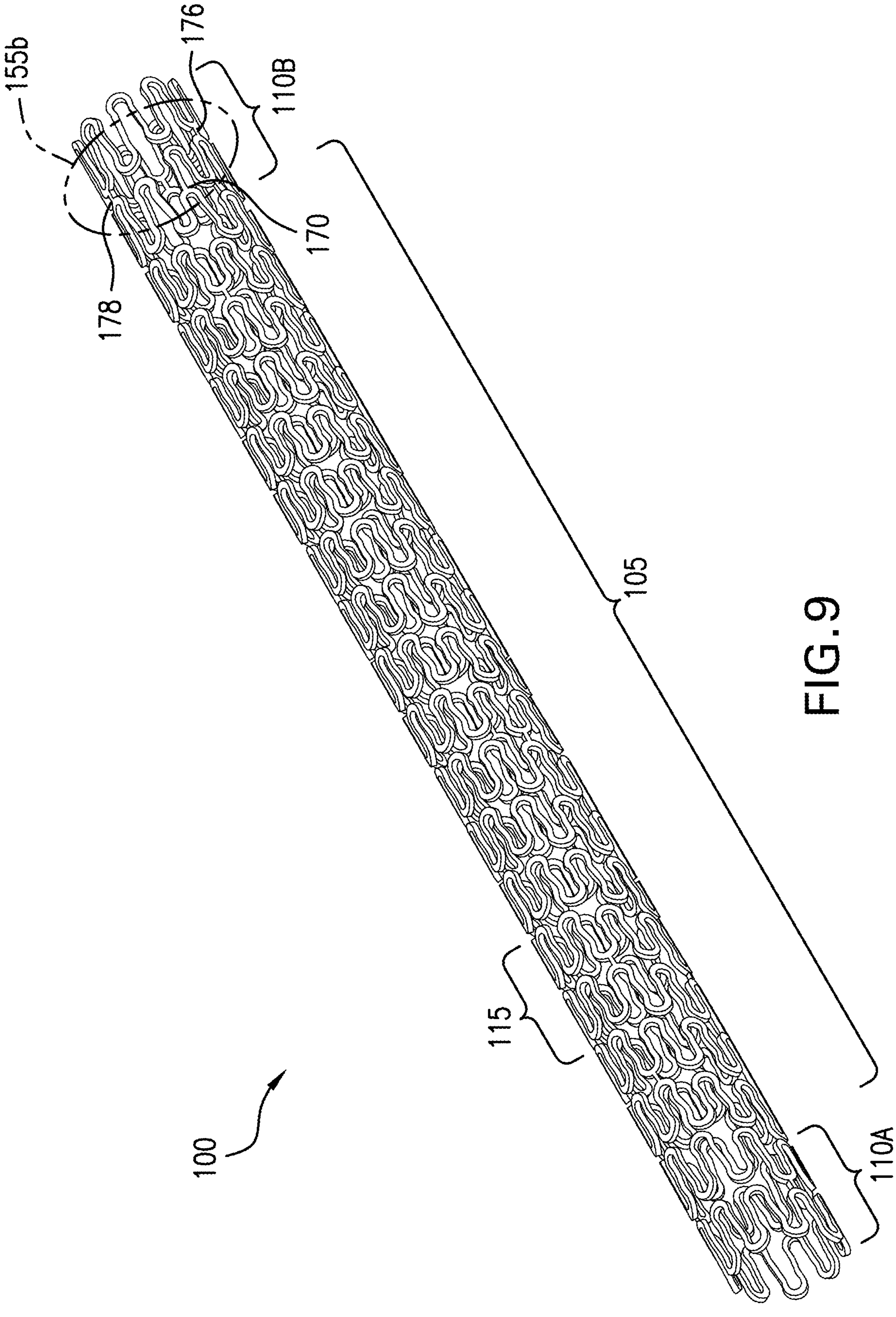
FIG. 9 illustrates a 3-dimensional model of the stent according to FIG. 8 from the third perspective and in the as-cut configuration.
Figure 10:
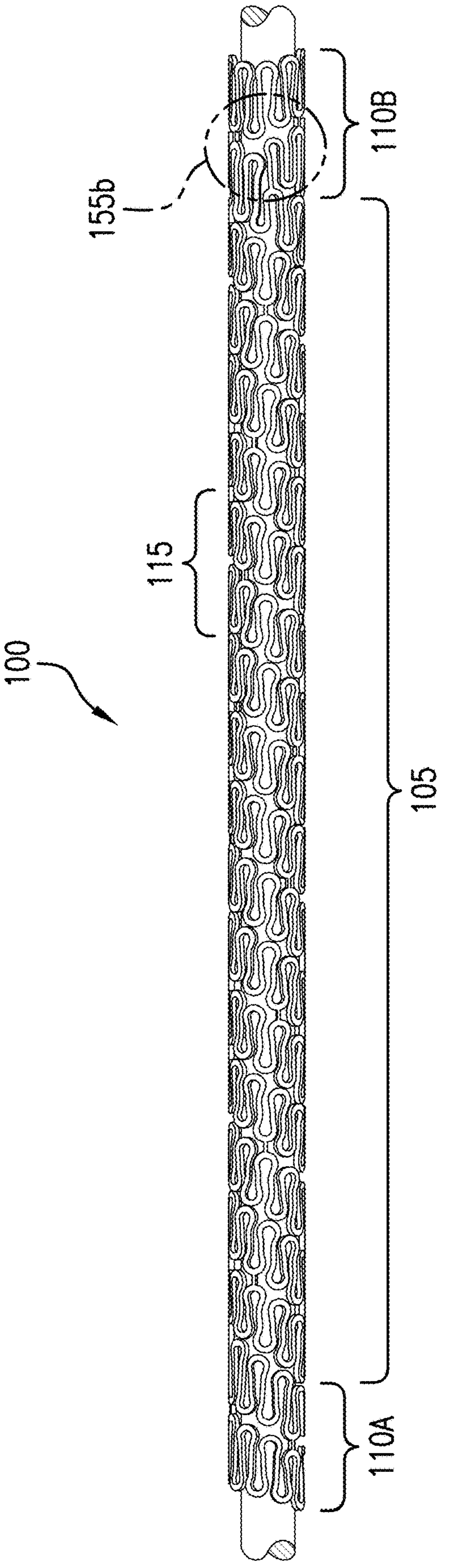
FIG. 10 illustrates the stent of FIG. 4 in a crimped, delivery configuration.
Figure 11:
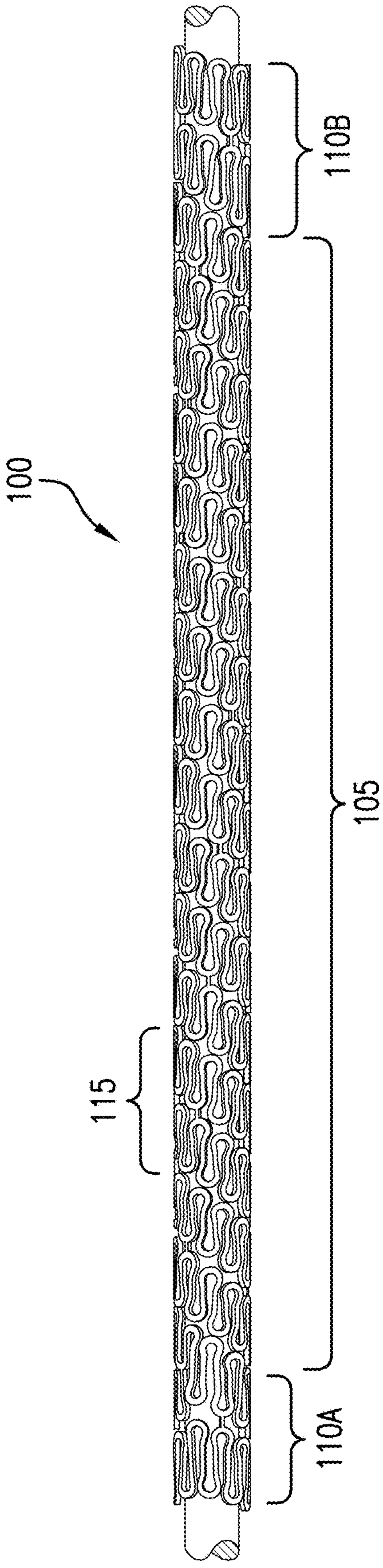
FIG. 11 illustrates the stent of FIG. 5 in the crimped, delivery configuration.
Figure 12:
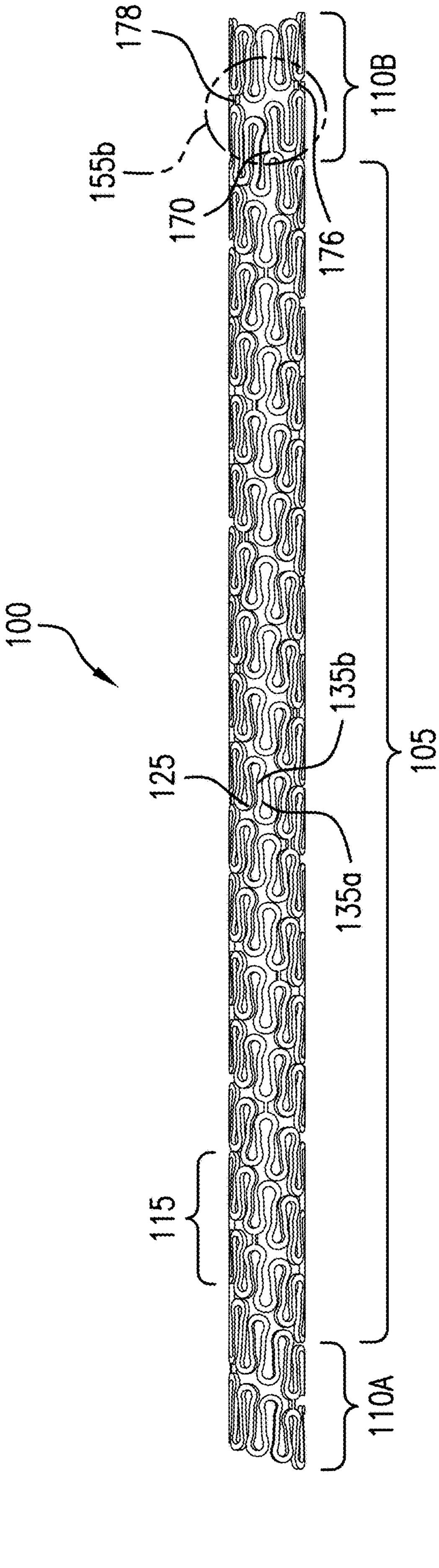
FIG. 12 illustrates the stent of FIG. 6 in the crimped, delivery configuration.
Figure 13:
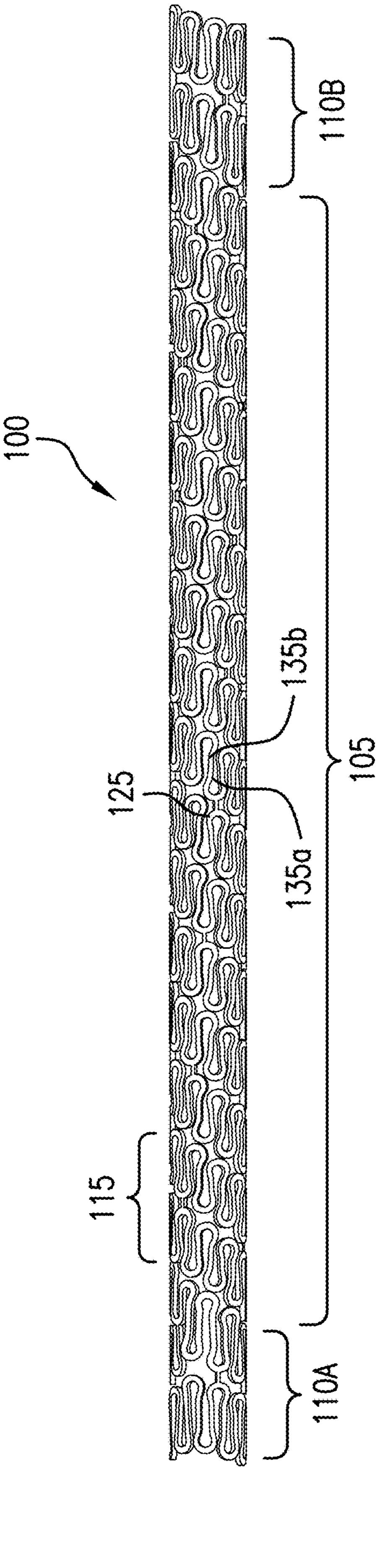
FIG. 13 illustrates the stent of FIG. 7 in the crimped, delivery configuration.
Figure 14:
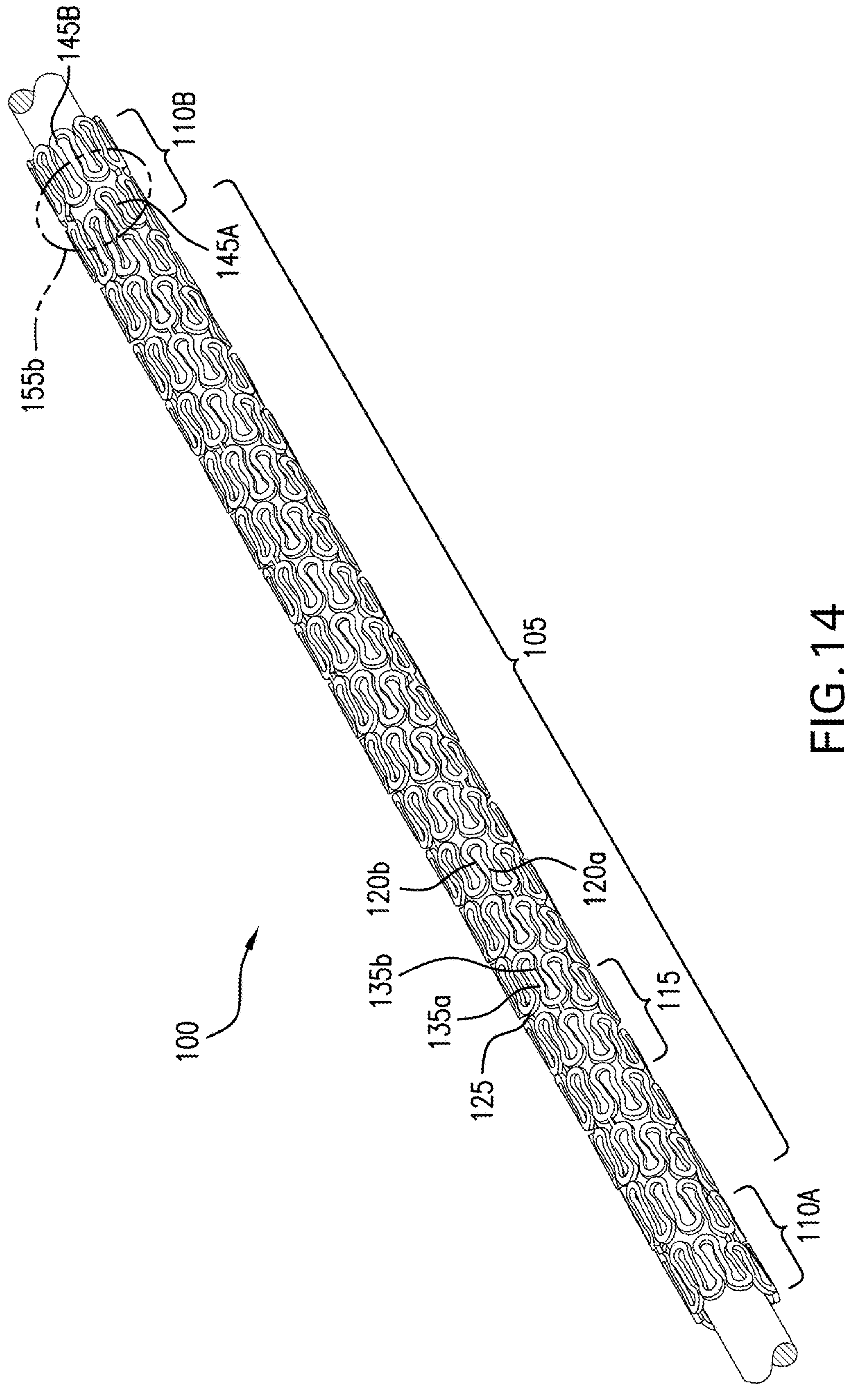
FIG. 14 illustrates the stent of FIG. 8 in the crimped, delivery configuration.
Figure 15:
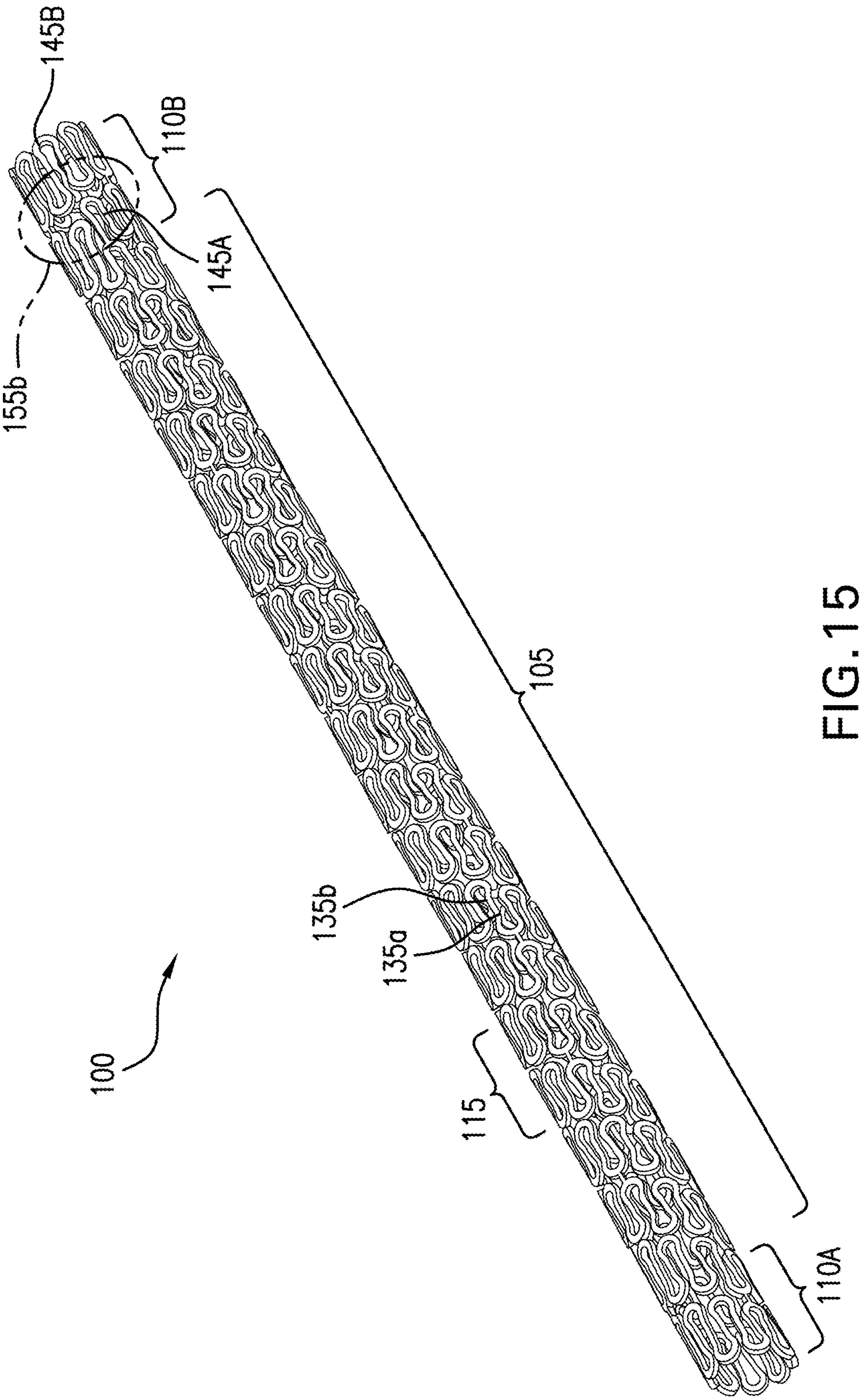
FIG. 15 illustrates the stent of FIG. 9 in the crimped, delivery configuration.
Figure 16:
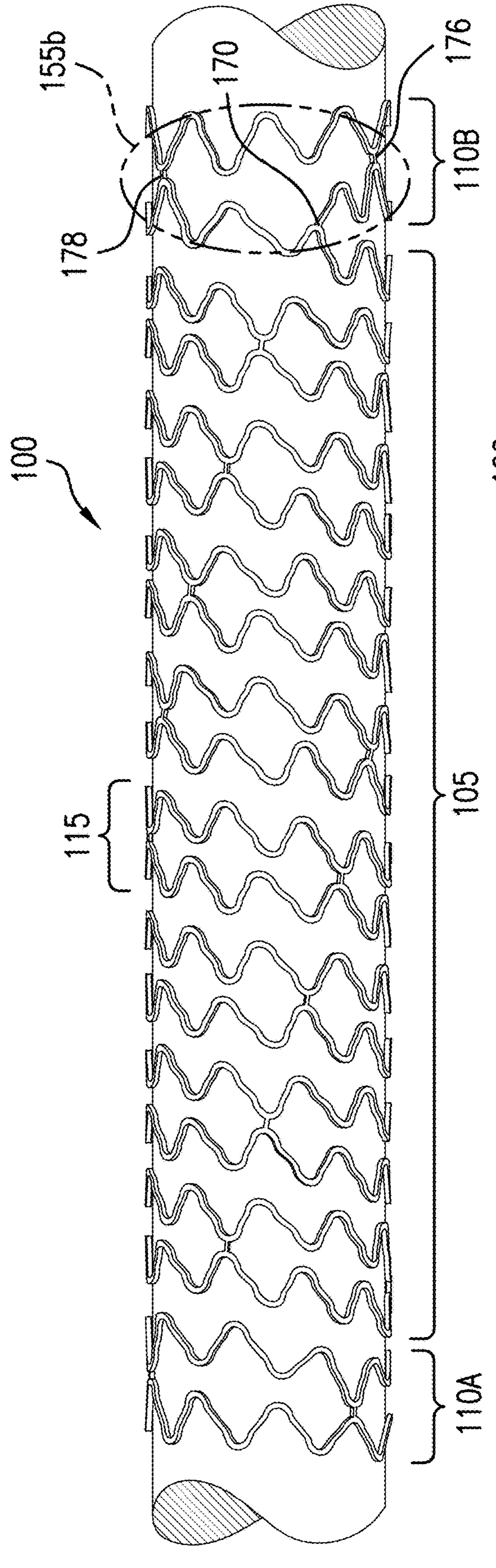
FIG. 16 illustrates the stent of FIG. 4 in an expanded, deployed configuration.
Figure 17:
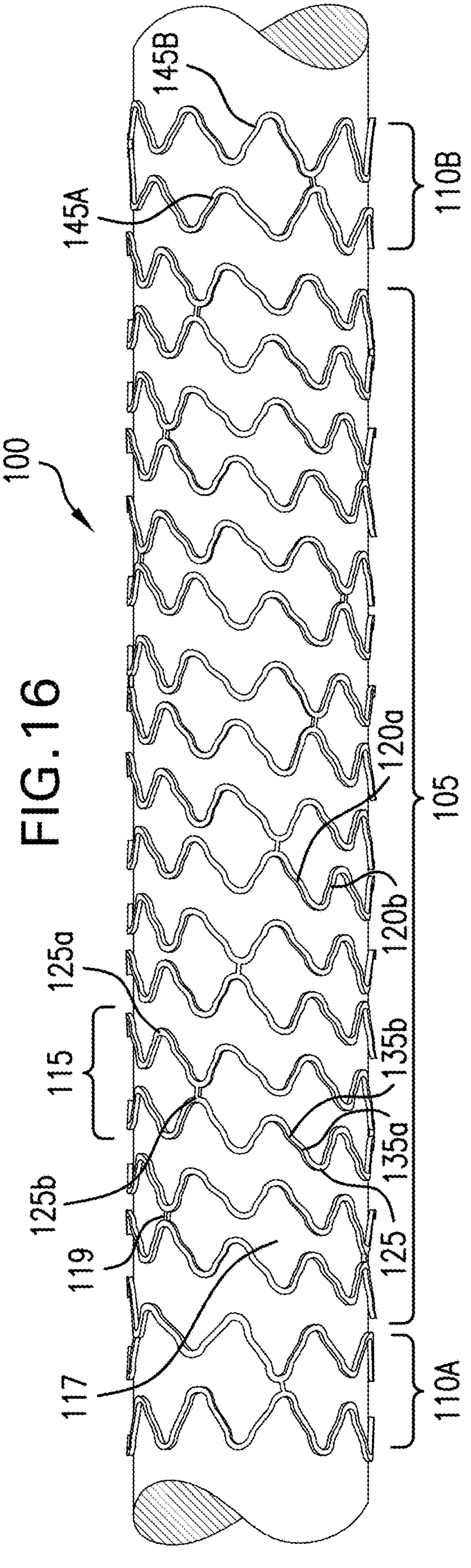
FIG. 17 illustrates the stent of FIG. 5 in the expanded, deployed configuration.
Figure 18:
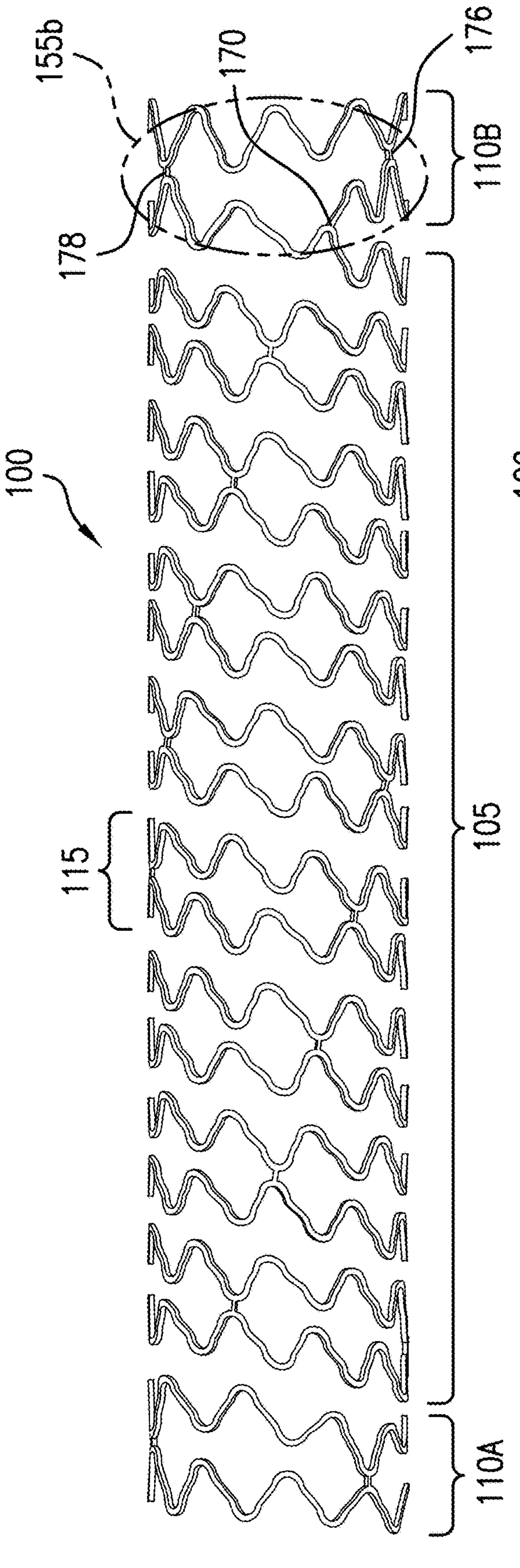
FIG. 18 illustrates the stent of FIG. 6 in the expanded, deployed configuration.
Figure 19:
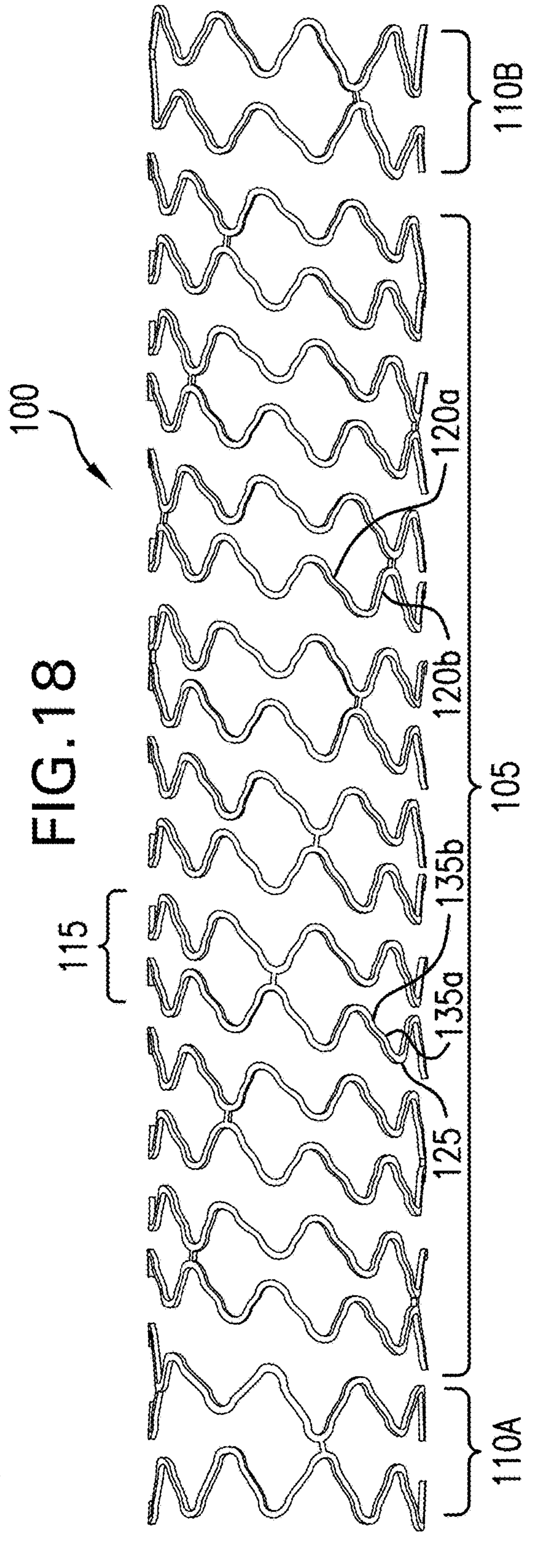
FIG. 19 illustrates the stent of FIG. 7 in the expanded, deployed configuration.
Figure 20:
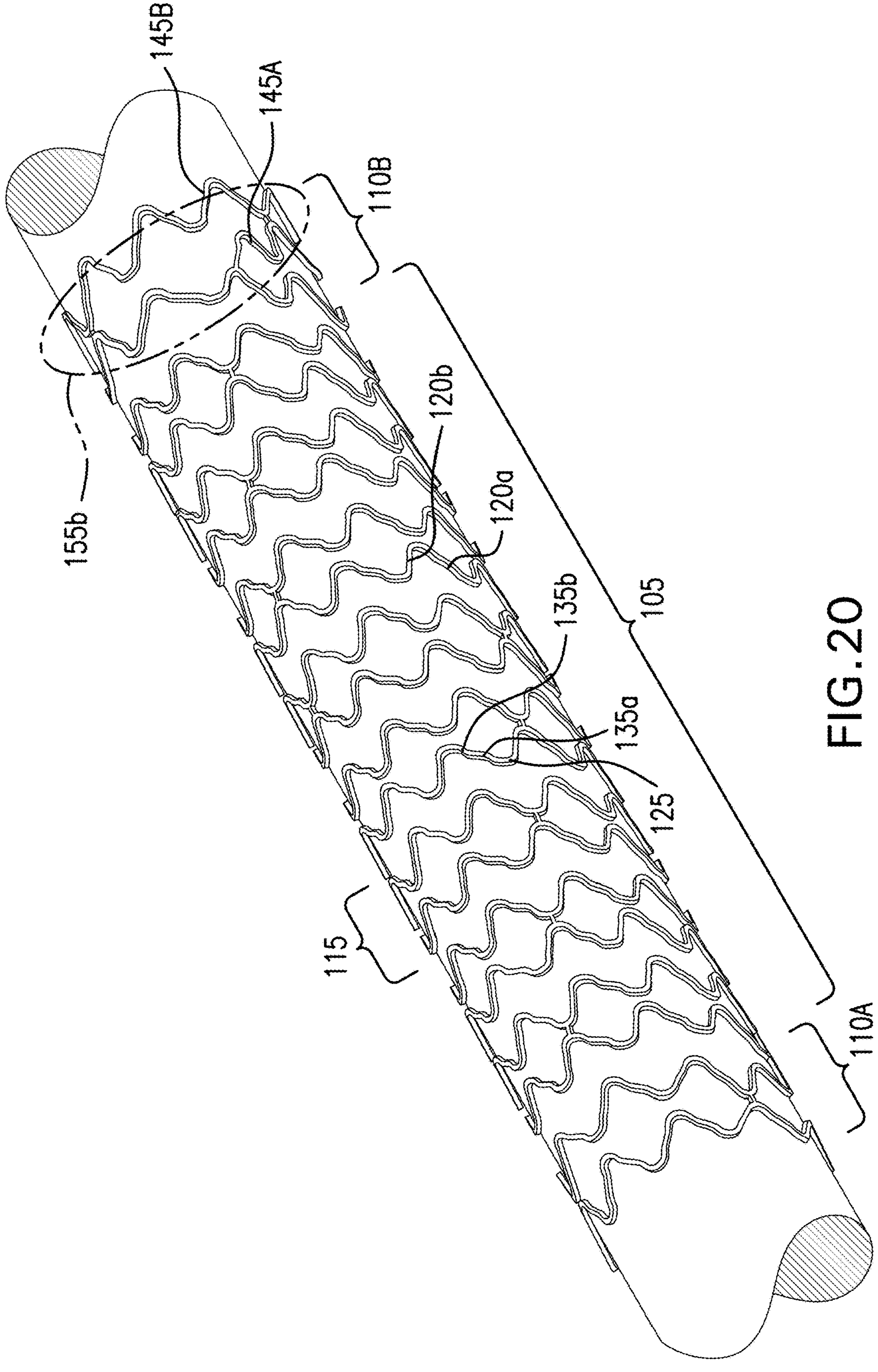
FIG. 20 illustrates the stent of FIG. 8 in the expanded, deployed configuration.
Figure 21:
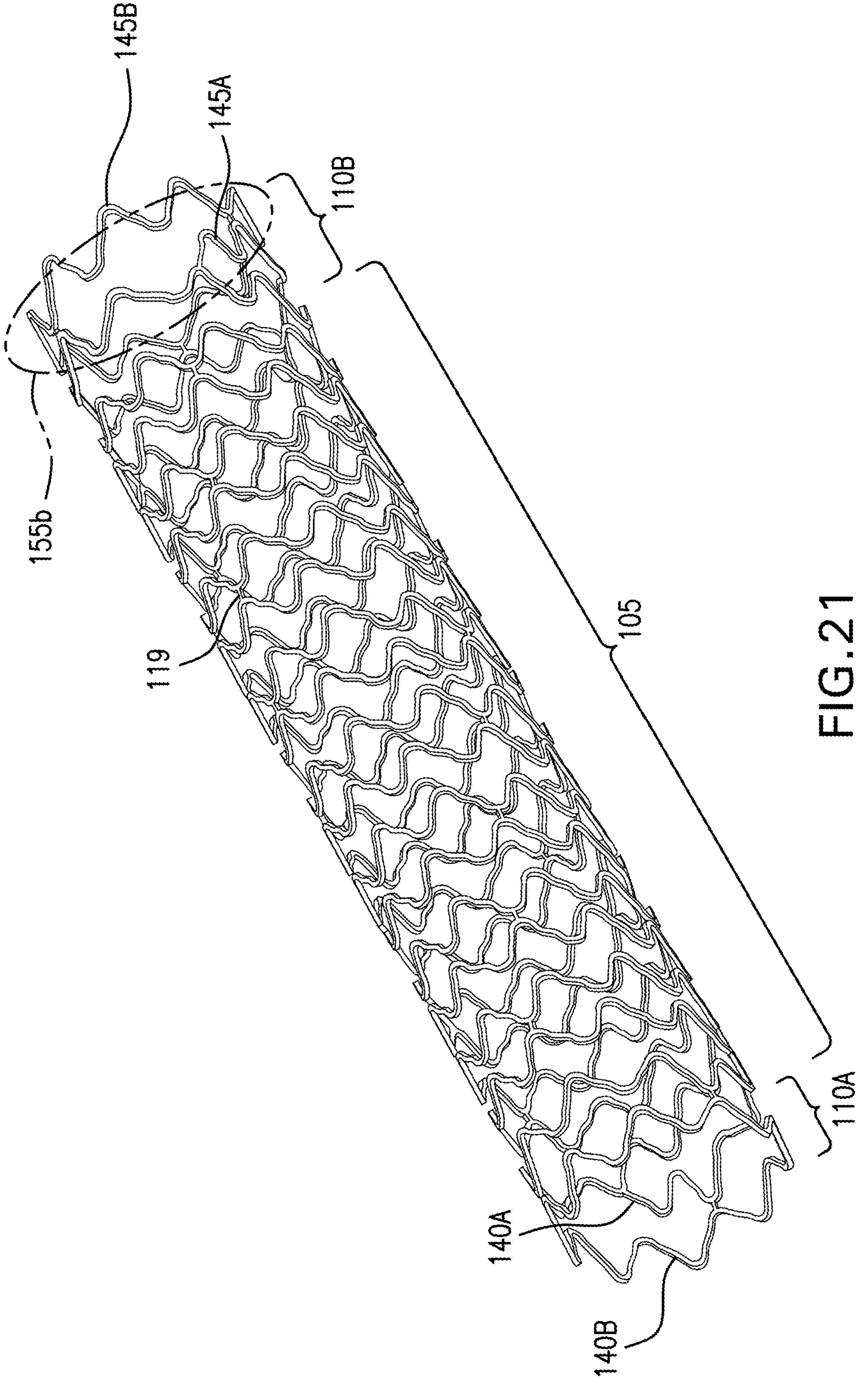
FIG. 21 illustrates the stent of FIG. 9 in the expanded, deployed configuration.

FIG. 3 illustrates an enlarged view of a pair of struts 122 connected to a loop 125 of a stent 100 in the as-cut configuration according to another embodiment of the invention. In some embodiments of the invention, each strut 120 of the pair of struts 122 may have the same length, where each strut 120 has the bent strut design. In the one embodiment shown in FIG. 3, a long strut 120*a* and a short strut 120*b* of a pair of struts 122 each has the bent strut design of the first and second bent sections 135*a-b*, and are connected to each other by a loop 125. The bent strut design 135*a-b* of the long strut 120*a* is substantially a mirror image of (or out-of-phase with) the bent strut design 135*a-b* of the short strut 120*b* of the pair 122. In the embodiment having a pair of struts 122 with the bent strut design as in FIG. 3, the pair of struts 122 with the bent strut design may be in an alternating or other uniform arrangement with a pair of struts 122 with a linear strut design or may be arranged in a random pattern. However, without departing from the scope or spirit of the invention, the bent strut design may be in only one strut 120 of the pair 122 and/or the pair of struts 122 may each be the same length. The stent of the embodiment shown in FIG. 3 may include all or some of the features in any combination, as described above and/or in relation to the embodiment shown in FIGS. 1-2. FIG. 3 illustrates an embodiment where the struts 120*a*-*b* have varying width from one end to the other, and where the loops 125 have a greater width than any portion of the struts 120*a*-*b* in order to optimally redistribute the stress/strain concentrations imparted on the stent 100 away from the loops 125 and toward the struts 120. As shown in FIG. 3, the width 139 of the loop 125 is about 98 microns, while the width of the struts 120*a*-*b* vary from about 79 to 83 microns. The width of the struts 120*a*-*b* may gradually decrease or taper from both ends toward a mid-section of the strut to redistribute the stress/strain forces away from the loop 125 and toward the midsection of the strut 120*a*-*b*.

Referring back to FIG. 1, the first and second ends 105*a*-*b* of the continuous component 105 includes first and second end rings 110A-B at the lengthwise ends 100*a*-*b* of the stent 100. The first end ring 110A may comprise at least one first circumferential end band 140A and at least one second circumferential end band 140B interconnected in the lengthwise direction L to form two interconnected circumferential end bands 140A-B at a lengthwise end 100*a* of the stent 100. Similarly, the second end ring 110B comprises at least one first circumferential end band 145A and at least one second circumferential end band 145B interconnected in the lengthwise direction L to form two interconnected circumferential bands 145A-B at the other lengthwise end 100*b* of the stent 100. Both of the two interconnected circumferential end bands 140A-B, 145A-B are substantially similar to the first and second bands 115A-B of the windings 115, except each of the two interconnected circumferential end bands 140A-B, 145A-B are oriented around a circumference of the stent 100 in the circumferential direction C, and are not arranged in the helical direction H. The two interconnected circumferential end bands 140A-B, 145A-B in the circumferential direction C form first and second end rings 110A-B oriented approximately at a right cylinder (forming a right or 90° angle with respect) to the lengthwise direction L of the stent 100. The lengthwise ends 100*a*-*b* of the stent 100 (at the end rings 110A-B) may have a straight cross-sectional profile. When the lengthwise ends 100*a*-*b* of the stent 100 are not straight (e.g., due to a non-uniform staggered or offset pattern of adjacent loops in the circumferential direction C), the lengthwise ends 100*a*-*b* have a non-uniform (e.g., a scalloped edge), which may be a random or periodic pattern.

With respect to the common features, the end rings 110A-B comprise, in the same manner as discussed with respect to the continuous component 105, one or more of the following exemplary features: the undulating pattern of loops connected to a pair of struts (including the in-phase or out-of-phase orientations), the variable (or non-variable) strut lengths, the staggered or offset pattern of adjacent loops, the bent strut design (including, but not limited to, the alignment and nestling arrangement between a loop and a bent section of a strut), redistribution of the stress/strain forces (such as a variable strut width, and/or loops having a different width relative to the strut width), the cellular design (including the number and/or interval of placement of links and/or direct connections) and/or any other combination of features, embodiments or configurations, such as described with respect to the continuous component 105.

The first and second end rings 110A-B extend from the winding 115 adjacent thereto. The transition from the winding 115 of the continuous component 105 to the first and/or second end rings 110A-B may result in one or more cells that are referred to as transition cells. The transition cell may be different than other cells (e.g., cells 117) of the stent 100 in that a transition cell may be formed or enclosed by at least a portion of the undulating pattern (i.e., struts and/or loops) of the first and/or second band 115A-B and by at least a portion of the undulating pattern (i.e., struts and/or loops) of the first and/or second circumferential end band 140A-B, 145A-B. Thus, the transition cells are enclosed by both the continuous component 105 and the first and/or second end rings 110A-B, rather than only by the continuous component 105, or only by the first or second end rings 110A-B.

Further, the area enclosed by a transition cell may be different in size and/or shape than the area enclosed by cells 117 of the continuous component 105 and/or cells formed between the two interconnected circumferential end bands 140A-B, 145A-B. The one or more transition cells between the first end ring 110A and an adjacent winding 115, and the one or more transition cells between the second end ring 110B and an adjacent winding 115 may be the same or different, for example, with respect to number, size, shape, orientation, location, and/or type of interconnection (e.g., links or direct connections). Further, in an embodiment having a plurality of transition cells between the first end ring 110A and an adjacent winding 115, the transition cells may be the same or different. Similarly, a plurality of transition cells between the second end ring 110B and an adjacent winding 115 may be the same or different.

FIG. 1 shows exemplary first, second and third transition cells 150, 155*a*, 155*b*, however, other transition cells having different sizes and/or configurations are within the scope of the present invention so long as the transition cell is formed between the continuous component 105 and the first or second end rings 110A-B. The transition between the continuous component 105 and the first or second end rings 110A-B may include any one or a combination of the exemplary first, second and third transition cells 150, 155*a*, 155*b* shown in FIG. 1 or other transition cells (not shown). The struts bordering the transition cells 150, 155*a*, 155*b* may have the same or variable lengths in order to enclose a desired area size and/or impart a desired flexibility or structural rigidity to the stent 100 at the transition between the continuous component 105 and the first or second end ring 110A-B, as is desired for a particular application. Some, all or none of the struts of the transition cells 150, 155*a*, 155*b* may include the bent strut design, the staggered or offset pattern of adjacent loops, and/or the redistribution of the stress/strain concentrations away from the loops (e.g., by struts having variable widths and/or loops having a greater width relative to the struts).

The first transition cell 150 is formed between the first end ring 110A and an adjacent winding 115 of the continuous component 105. The first transition cell 150 is enclosed by a portion of the undulating pattern of the first band 115A, the second band 115B and the first circumferential end band 140A. The first transition cell 150 is enclosed by an interconnection 160 (e.g., direct connection) between the first circumferential end band 140A (e.g., at a strut thereof) and the first band 115A (e.g., at an apex of a valley 125*b* thereof). The first transition cell 150 is also enclosed by an interconnection 162 (e.g., a link 119) between the first band 115A (e.g., at an apex of a valley 125*b* thereof) and the second band 115B (e.g., at an apex of a valley 125*b* thereof). Further, the first transition cell 150 is enclosed by an interconnection 164 (e.g., a direct connection) between the second band 115B (e.g., at a strut 120 thereof) and the first circumferential end band 140A (e.g., at an apex of a peak thereof). In the illustrative embodiment shown in FIG. 1, the first transition cell 150 is bordered by six struts 120 of the first band 115A connected by five free loops 125 of the first band 115A, one strut 120 of the second band 115B, and six struts of the first circumferential end band 140A connected by five loops of the first circumferential end band 140A.

The second transition cell 155*a* is substantially similar to the first transition cell 150, but is formed between the second end ring 110B and an adjacent winding 115 of the continuous component 105. The second transition cell 155*a* is enclosed by a portion of the undulating pattern of the first band 115A, the second band 115B and the first circumferential end band 145A. The second transition cell 155*a* is enclosed by an interconnection 170 (e.g., direct connection) between the first circumferential end band 145A (e.g., at a strut thereof) and the second band 115B (e.g., at an apex of a valley 125*b* thereof). The second transition cell 155*a* is also enclosed by an interconnection 172 (e.g., a link 119) between the first band 115A (e.g., at an apex of a valley 125*b* thereof) and the second band 115B (e.g., at an apex of a valley 125*b* thereof). Further, the second transition cell 155*a* is enclosed by an interconnection 174 (e.g., a direct connection) between the first band 115A (e.g., at a strut 120 thereof) and the first circumferential end band 145A (e.g., at an apex of a peak thereof). The second transition cell 155*a* is bordered by six struts 120 of the second band 115B connected by five free loops 125 of the second band 115B, one strut 120 of the first band 115A, and six struts of the first circumferential end band 145A connected by five loops of the first circumferential end band 145A.

The third transition cell 155*b* is formed between the second end ring 110B and an adjacent winding 115 of the continuous component 105. The third transition cell 155*b* is enclosed by a portion of the undulating pattern of the second band 115B, the first circumferential end band 145A and the second circumferential end band 145B. The third transition cell 155*b* is enclosed by an interconnection 176 (e.g., a link) between the first circumferential end band 145A (e.g., at an apex of a valley thereof) and the second circumferential end band 145B (e.g., at an apex of a valley thereof). The third transition cell 155*b* is also enclosed by an interconnection 178 (e.g., a link) between the second band 115B (e.g., at an apex of a valley 125*b* thereof) and the second circumferential end band 145B (e.g., at an apex of a valley thereof). Further, the third transition cell 155*b* is enclosed by the interconnection 170 (e.g., a direct connection) between the first circumferential end band 145A (e.g., a strut thereof) and the second band 115B (e.g., at an apex of a valley 125*b* thereof). The third transition cell 155*b* is bordered by six struts of the second circumferential end band 145B connected by five free loops of the second circumferential end band 145B, four struts 120 of the second band 115B connected by three loops 125, and three struts of the first circumferential end band 145A connected by two loops of the first circumferential end band 145A. In another embodiment (not shown), a transition cell similar to the third transition cell 155*b* may be similarly formed between the first end ring 110A and an adjacent winding 115, where this transition cell may be enclosed by the first band 115A, the first circumferential end band 140A and the second circumferential end band 140B.

The stent according to embodiments disclosed herein may be useful for coronary or non-coronary applications such as a peripheral stent, a brain stent or other non-coronary applications. For coronary use, the stent may vary in length from 6-60 mm, have an expanded, deployed outside diameter of 1.5-5.5 mm, and a compressed, delivery outside diameter of 0.7-1.2 mm. For non-coronary use (e.g., peripheral applications), the stent may vary in length from 20-250 mm, have an expanded, deployed diameter of 3-8 mm, and a compressed, delivery diameter of 0.7-2.0 mm. Further for coronary use, the stent may have a cell design with fewer interconnections (e.g., links or direct connections) and thus larger cells in order to provide a stent having cells sufficiently large for increased side branch access which is advantageous for use in the tortuous coronary vessels having multiple side branches. The cells of the stent may be the same or similar size along substantially the entire length of the stent or at least along the main body of the stent (excluding the ends) in order to provide similar side branch access and support throughout. In the illustrative embodiment shown in FIG. 1, each winding 115 of the stent 100 has three interconnections and nine peaks or crowns 125*a*. However, any other number of interconnections or peaks may be selected for a particular application and desired stent size. For example, in another embodiment, each winding may have two interconnections and six peaks or crowns, thereby forming a smaller diameter stent.

FIGS. 4-21 illustrate a 3-dimensional of the stent 100 according to the embodiment shown in FIG. 3. FIGS. 4-9 illustrate the as-cut configuration of the stent 100 from different perspectives, FIGS. 10-15 illustrate the crimped, delivery configuration of the stent 100 from different perspectives, and FIGS. 16-21 illustrates the expanded, deployed configuration of the stent 100 from different perspectives.

The features of the present invention described herein, individually or in combination, advantageously achieve an enlarged expanded outside diameter and/or a reduced compressed outside diameter compared to conventional stents. For example, in embodiments of the present invention having a combination of long and short struts, an enlarged expanded diameter may be achieved by the long struts. A reduced compressed diameter may be achieved, for example, by the bent strut design contributing to the nestled arrangement in the crimped configuration of the stent. Alternatively or in addition, other features which may further contribute to a reduced compressed diameter include, for example, the staggered or offset pattern of loops which may result from helically orientated windings and/or variable length struts, for example. Further, compared to conventional stents, the stent of the present invention advantageously maximizes the distance between adjacent struts, thereby minimizing the interaction there-between, where such interaction may be harmful to the stent, the stent coating and/or the inner balloon.

The embodiments shown in FIGS. 4-21 are substantially similar to the embodiment shown in FIGS. 1-2, except all of the struts 120 of the continuous component 105 and of the first and second end rings 110A-B have the bent strut design of the first and second bent sections 135*a-b*. It should be noted, that in any of the embodiments of the present invention, the stent 100 may include the bent strut design in all, some or one strut depending, for example, on the particular application and/or desired expanded or compressed stent diameter size.

Further, similar to FIG. 1, the embodiments shown in FIGS. 4-21 include the windings 115 comprising the two interconnected bands 115A-B, and the two interconnected circumferential end bands 140A-B, 145A-B at the lengthwise ends 100*a-b* of the stent 100. The embodiments shown in FIGS. 4-21 also illustrate the staggered or offset pattern of adjacent loops 125 in the helical direction H, as similarly described with respect to FIG. 1, as well as struts 120*a-b* of variable length. Also similar to FIG. 1, FIGS. 4-21 show the cellular design of cells 117 and links 119, however as described above, the some or all of the links 119 may be replaced by direct connections or other connection means. The stent 100 of FIGS. 4-21 may also include the optimal redistribution of the stress/stain concentrations as discussed above, where, for example, all, some or one of the loops 125 may have a width wider than the struts 120 and/or all, some or one of the struts 120 may have a variable width along the strut length. Additionally, the embodiment of FIGS. 4-21 may include one or more transition cells, as discussed above. For example, the third transition cell 155*b* is shown in FIGS. 4, 6, 8-10, 12, 14-16, 18, and 20-21. The stent 100 of FIGS. 4-21, as well as of any of the other embodiments described herein, may have one, some or all of the features described herein.

FIGS. 4-9 illustrate the stent 100 in the as-cut configuration. The as-cut configuration of the stent 100 is the manufactured profile of the stent 100 when laser cut from a tube or when laser cut or chemically etched from a flat metal sheet which is then rolled into and secured as the tubular form. The outside diameter of the stent 100 in the exemplary as-cut configuration of FIGS. 4-9 is smaller than in the expanded, deployed configuration of FIGS. 16-21 and larger than in the crimped, delivery configuration of FIGS. 10-15, however, it is understood that the stent of the invention may be cut to any desired outside diameter for the as-cut configuration.

As shown in FIGS. 4-9, at least one strut 120 of the stent 100 includes the bent strut design of the first and second bent sections 135*a-b*. Further, as shown in FIGS. 4-9, loops 125 in the helical direction H are arranged in a non-overlapping (e.g., staggered) relationship. That is, loops 125 are aligned with struts 120 in the helical direction H. In particular, a bent section 135*a-b* of a strut 120 is aligned with an adjacent loop 125 in the helical direction H. In the as-cut configuration, the loops 125 are aligned but distanced from the bent sections 135*a-b*, such that the loops 125 are not yet nestled in the opposing bent sections 135*a-b*.

FIGS. 10-15 illustrate the stent 100 in the crimped, delivery configuration (or partially crimped configuration). The outside diameter of the stent 100 in the crimped (or partially crimped) configuration is smaller than in the expanded, deployed configuration. In the crimped configuration, the struts 120 move closer to each other when the stent 100 is compressed onto a catheter, such as a balloon or an expandable member of a catheter. Alternatively or in addition, a radius of curvature of the loops 125 may decrease as the stent 100 is compressed to the crimped configuration.

As shown in FIGS. 10-15, at least one strut 120 of the stent 100 includes the bent strut design of the first and second bent sections 135*a-b*. Because loops 125 are aligned with the bent sections 135*a-b* of the struts 120, the crimping process moves a loop 125 toward the complementary shaped opposing bent section 135*a-b* of an adjacent strut 120 in the helical direction H, thereby achieving the nestled arrangement. The stent 100 is able to more tightly crimp than a conventional stent because of the achieved nestled arrangement in the crimped profile, where the bent sections 135*a-b* do not substantially straighten during or when compressed. In particular, stent 100 is able to more tightly crimp than conventional stents because the bent section 135*a-b* creates a space in which the adjacent loop 125 may nestle. The space created results in a bent shape 130 where an inner distance between a pair of struts 122 is reduced at the inward curvature of the strut 120. As shown in FIGS. 10-15, a loop 125 is tightly crimped or compressed into contact with, or near contact with, a first or second bent section 135*a-b*. The loop 125 is offset from an adjacent loop (to form offset loops in the helical direction H), such that the loop 125 is positioned proximal with respect to a loop above and distal with respect to a loop below, or vice versa, and therefore interference between adjacent loops 125 are avoided.

In one embodiment, first and/or second bent sections 135*a-b* maintain the same amount of curvature as in the as-cut configuration (or expanded configuration), such that as the struts 120 move closer to each other during or when compressed (onto a guide catheter) the curvature of the first and/or second bent sections 135*a-b* do not change. In another embodiment, during or when crimped, the first and/or bent sections 135*a-b* become more bent, such that curvature of the first and/or second bent sections 135*a-b* increases, and thereby further reduces the compressed diameter of the stent 100. In yet another embodiment, during or when crimped, the first and/or second bent sections 135*a-b* become less bent but maintain at least some amount of curvature and do not substantially straighten in order to allow for the nestled arrangement of struts and loops.

FIGS. 16-21 illustrate the stent 100 in the expanded, deployed configuration (or partially expanded configuration). The outside diameter of the stent 100 in the expanded (or partially expanded) configuration is larger than in the crimped, delivery configuration. In the embodiments shown in FIGS. 16-21, the stent 100 is expanded or deployed to a 3.0 mm outside diameter, however other diameters may be possible as suitable for a particular application. In the deployed configuration, as the stent 100 is expanded by a guide catheter, such as a balloon or expandable member of a catheter, or is self-expanded, the struts 120 move away from each other so that a radius of curvature of the loops 125 is increased.

As shown in FIGS. 16-21, at least one strut 120 of the stent 100 includes the bent strut design of the first and second bent sections 135*a-b*. Further, as shown in FIGS. 16-21, the loops 125 in the helical direction H remain in the non-overlapping (e.g., staggered) relationship, where loops 125 are aligned with (but distanced from) the bent section 135*a-b* of the struts 120.

In one embodiment, first and/or second bent sections 135*a-b* maintain the same amount of curvature as in the as-cut configuration or crimped configuration such that, as the struts 120 move away from each other during or when expanded, the curvature of the first and/or second bent sections 135*a-b* do not change. In another embodiment, during or when expanded, the first and/or bent sections 135*a-b* become more bent, such that curvature of the first and/or second bent sections 135*a-b* increases. In yet another embodiment, during or when expanded, the first and/or second bent sections 135*a-b* become less bent but maintain at least some amount of bend or curvature and do not substantially straighten. In still a further embodiment, during or when expanded, the first and/or second bent sections 135*a-b* straighten or substantially straighten, thereby further enlarging the expanded diameter of the stent 100.

Figure 22:
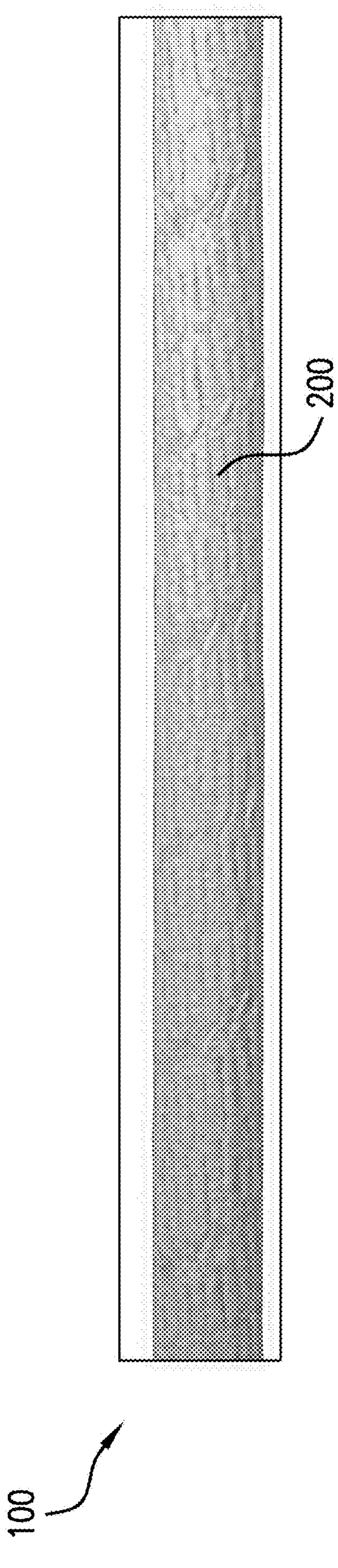
FIG. 22 illustrates a stent, in a tubular view, according to any of the embodiments of the present invention in a crimped configuration and having a polymer coating.
Figure 23:
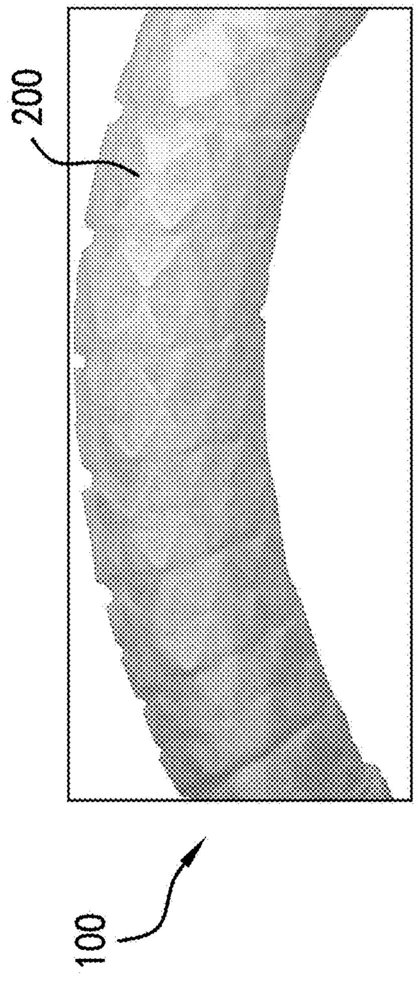
FIG. 23 illustrates a stent, in a tubular view, according to the embodiment of FIG. 22 in a radially expanded configuration and having a polymer coating.

FIGS. 22-23 depict the stent 100, according to any of the embodiments discussed herein, with an optional polymer coating 200. The polymer coating 200 may be made from or include a biodegradable or biocompatible polymer and/or may include a drug, for example, in a formulation. Moreover, the polymer coating 200 may be in the form of a fiber mesh. The polymer coating 200 may be applied by, for example, electrospinning, physical vapor deposition (PVD), chemical vapor deposition (CVD), thermal evaporation, sputtering, spray coating or other methods known in the art. The polymer coating 200 may be applied to all or a portion of the stent 100 in a continuous or non-continuous manner, and may or may not embed the stent 100. In one embodiment, the polymer coating 200 may be applied or extends in a gap between adjacent windings 115 and/or in a gap formed by a cell 117. The elastic range of the polymer coating 200 (e.g., mesh of fibers) is preferably sufficient to allow expansion of the stent 100 and maximal bending during and after implantation without reaching the elastic limit. Further, the polymer coating 200 may be substantially porous such that blood flow and nutrient flow is permitted therethrough or the polymer coating 200 may be applied to the stent 100 in a manner permitting the stent 100 to be a substantially porous structure (i.e., not fluid-tight). The porosity value of the polymer coating 200 is substantially greater than that of a graft material used in graft or stent-graft devices which are substantially fluid-tight. Alternatively, the material of the polymer coating 200 may be entirely non-porous, but may be made (e.g., punctured) to include openings for blood and nutrient flow and/or side branch access, for example.

In one embodiment, the polymer coating 200 may be formed as a continuous sheet of polymer material over the stent 100. The continuous sheet may be a porous sheet enveloping an outer surface of the stent or embedding the stent therein. The polymer coating 200 may be made porous through pores and/or fenestrations formed on the continuous sheet. The pores and/or fenestrations may or may not be irregularly shaped, and may or may not be uniformly distributed throughout the stent 100. The pores and/or fenestrations may be formed on portions of the continuous sheet which do not envelop or embed the metallic components (e.g., struts 120 and loops 125) of the stent 100. The size of the pores may be in a range of 2.0 to 500 microns, and the size of the fenestrations may be larger than the pores. In another embodiment, the polymer coating 200 may be a mesh of fibers having a porous structure permitting fluid flow therethrough. The mesh of fibers may themselves be porous or may be arranged at variable distances (e.g., interstices) to provide for the non-fluid tight stent 100. The polymer may interconnect unconnected adjacent helical windings of the stent. In any of the above embodiments, the polymer may interconnect one or a plurality of windings of the stent. In some embodiments, the polymer interconnects every winding of the stent. The polymer coating 200 may be easily pierced, by for example a catheter or guidewire tip, to allow for side branch access. The polymer coating 200 may be applied in-between metallic portions of the stent 100 and/or may be coated onto the metallic portions of the stent 100 such as coated onto the stent struts. One skilled in the art recognizes methods of coating, e.g., as described in U.S. Pat. No. 7,959,664 entitled "Flat Process of Drug Coating for Stents" the entire contents of which are incorporated herein by reference.

The stent of the invention may be formed from metals, polymers, other flexible materials and/or other biocompatible materials. The stent may be constructed of stainless steel, cobalt chromium ("CoCr"), platinum chromium, NiTinol ("NiTi") or other known materials or alloys. The stent pattern or design as described herein may be etched or laser cut into a flat metal ribbon or a flat panel. Alternately, the stent may be made from a tube wherein the stent pattern or design has been etched or laser cut into it. In either case, the stent will have a pattern resembling the embodiments described herein and will resemble a metal wire. It is also contemplated that the stent may be formed from helically winding a flat strip or wire having the stent pattern or design described herein. In one embodiment, the invention contemplates wrapping or embedding the stent with a biocompatible polymer such that the polymer may structurally support the stent but does not limit longitudinal and/or twisting movement of the stent, thereby forming a stent with high radial strength and high longitudinal (i.e., lengthwise) flexibility.

The stent of the invention may be balloon expandable or self-expanding. When a balloon-expandable stent system is used to deliver the stent, the stent is crimped on a balloon at the distal end of a catheter assembly which is then delivered to the implantation site, for example a coronary artery, using techniques well-known in the field of interventional cardiology. The balloon is then inflated, radially applying a force inside the stent and the stent is expanded to its working diameter. Alternatively, the stent may be self-expanding in which case the stent is held in a restricted diameter before and during delivery to the implantation site using mechanical means, for example a sleeve. When the stent is positioned in the implantation site, the sleeve is removed and the stent expands to its working diameter.

The stent may be arranged to provide a cellular stent design, where the cells are formed between the first and second bands, between a helical band and a circumferential end band, and/or between first and second circumferential end bands. Example designs are described in, but not limited to, U.S. Pat. No. 6,723,119, which is incorporated herein in toto, by reference. Another example design is a stent pattern described in U.S. Pat. No. 7,141,062 ("'062"). The '062 stent comprises triangular cells, by which is meant a cell formed of three sections, each having a loop portion, and three associated points of their joining forming each cell. One or more rows of such cells may be assembled in a ribbon which may be helically coiled from the stent. Similarly, the cells in the stent described in U.S. Pat. No. 5,733,303 to Israel et al. ("'303") may be used for the stent but helically coiled. The '303 patent describes a stent having cells formed of four sections, each having a loop portion and four associated points of their joining forming each cell, also known as square cells. Such square cells may be formed with the first and second bands and links of the stent of the present invention. Each of these designs is expressly incorporated herein in toto by reference. Other similarly adaptable cellular stent designs known in the art are readily applicable to the helical stent of the present invention, such as diamond shaped cells or non-diamond shaped cells.

A basecoat may optionally be applied to the stent of the present invention. The basecoat is applied on the metallic structure of the stent and prior to applying the optional polymer coating or material. The basecoat may promote the joining of the optional polymer material to the stent. The basecoat may be applied or affixed to the stent through a variety of means, for example, rolling, dip coating, spray coating or the like. The basecoat may be a polymer, such as a bio-stable or a biodegradable polymer. The bio-stable polymer used for the basecoat may be a polyurethane or an acrylate type polymer. The biodegradable polymer used for the basecoat may be the same or different than the biodegradable polymer used to wrap or embed the stent, such as the polymer coating 200 of FIGS. 22-23. The polymer for the basecoat is selected to be adhesive to the metallic structure of the stent at specific conditions, while the polymer for wrapping or embedding the stent may adhere to the basecoat at different conditions. The polymer for the basecoat may be dissolvable in most solvents and should be flexible enough to withstand significant deformations during and after stent deployment.

The polymer used to optionally wrap or embed the stent, such as the polymer of FIGS. 22-23, can be disposed within parts of the stent or embedded throughout the stent and it may support the stent structure partially or fully. The polymer is made from a biocompatible material. Biocompatible material may be a durable polymer, such as polyesters, polyanhydrides, polyethylenes, polyorthoesters, polyphosphazenes, polyurethane, polycarbonate urethane, silicones, polyolefins, polyamides, polycaprolactams, polyimides, polyvinyl alcohols, acrylic polymers and copolymers, polyethers, celluiosics and any of their combinations or combination of other polymers in blends or as copolymers. Of particular use may be silicone backbone-modified polycarbonate urethane and/or expanded polytetrafluoroethylene (ePTFE). Alternatively, the biocompatible material may be a biodegradable polymer. The polymer may be a porous mesh of polymer fibers. The polymer may further include an anti-proliferative drug which inhibits growth of smooth muscle cells and helps prevent restenosis (re-narrowing of the vessel) at the stent implantation site. The combination of drug and polymer offers the advantage of controlled drug elution over a predetermined period of time (e.g., 30, 60, or 90 days) depending on the requirements of a particular procedure and the technical characteristics of the polymer. The drug elution may be controlled by, for example, the selection of the polymer or blend of polymer(s) and drug, the polymer mesh dimensions, fiber diameter or fiber structure, or any structural feature which affects the coefficient of diffusion. The biodegradable polymer may be selected so as to completely biodegrade within the vessel wall over a predetermine period of time and after drug elution has completed. The biodegradable polymer may be selected from the group consisting of: polyglycolide, polylactide, polycaprolactone, polydioxanone, poly(lactide-co-glycolide), polyhydroxybutyrate, polyhydroxyvalerate, trimethylene carbonate, polyphosphoesters, polyphosphoester-urethane, polyaminoacids, polycyanoacrylates, fibrin, fibrinogen, cellulose, starch, collagen, hyaluronic acid and blends, mixtures and copolymers thereof.

The stent according to the invention may optionally incorporate one or more drugs that will inhibit or decrease smooth muscle cell migration and proliferation, and reduce restenosis. Examples of such drugs include for example rapamycin, paclitaxel, sirolimus, everolimus, zotarolimus, ridaforolimus, biolimus, and analogs thereof. The drug may be provided on the metallic stent (e.g., struts and/or loops) and/or on the polymer material or coating (e.g., polymer coating 200 of FIGS. 22-23). For example, the drug may be provided as a partial or complete coating over the stent 100 and/or the polymer coating 200. The metallic stent may be surface-treated to have abnormalities (e.g., indentations, wells or fenestrations) which may house the drug therein or thereon. Alternatively or in addition, the polymer material may have abnormalities (e.g., indentations, wells or fenestrations) for housing the drug therein or thereon.

In an embodiment, the drug may be selectively "printed" on targeted regions of the stent and/or polymer. In one embodiment, the drug may be confined to and/or provided on only those regions subjected to lower mechanical strain after implantation. In one embodiment, the drug or drug/polymer formulation is deposited or printed using an inkjet technique. An inkjet device includes an inkjet head with a small orifice. When voltage is applied to the inkjet device, it contracts for a period of milliseconds and spits out a small drop of desired product (e.g., drug or drug/polymer formulation). The drop diameter is adjustable and varied, and moving the inkjet head or the target object (e.g., stent) provides for the selective and precise product deposition/printing.

It is desirable to design the structure of the stent such that after neo-intimal growth and "embedding" of the stent struts in the tissue, the stent does not interfere with vasomotion of the blood vessel in which it is implanted. This reduction or elimination in interference is achieved by reducing the mechanical resistance of the stent to bending/twisting (i.e., via the stent design and/or the polymer coating). The exemplary stent configurations described herein provide metallic stents which support the blood vessel radially, but impose minimal mechanical constraint longitudinally and torsionally. Specifically, the inventive stent imposes minimal mechanical constraint on the transverse flexion, torsion, elongation and vasodilatation/vasoconstriction of the blood vessel.

It is also noted that while the structural components of the stent of the present invention are not separate structures and are formed integral to each other (via, e.g., laser cutting or chemical etching) to form the continuous tubular shape of the stent of the present invention, the structural components, such as the interconnected bands, struts, loops, links, and/or end rings, among other features have been referred to separately for ease of identification and discussion. Further, it should be noted that reference to the same reference numerals in different drawings indicate the same features.

It should be understood that the above description and drawings are only representative of illustrative examples of embodiments. For example, it is understood that the bent strut design described herein, which contributes to the nestled arrangement for reducing the compressed diameter of the stent, may be incorporated in any appropriate intraluminal endovascular devices (e.g., a stent, graft or stent-graft device) as desired, including, for example, a stent having any number of bands within a winding. For the reader's convenience, the above description has focused on a representative sample of possible embodiments, a sample that teaches the principles of the invention. Other embodiments may result from a different combination of portions of different embodiments. The description has not attempted to exhaustively enumerate all possible variations.

What is claimed is:

1. An endovascular device, comprising:

a continuous component having a tubular shape and extending from a first end to a second end along a lengthwise direction of the endovascular device, wherein the continuous component comprises:

a plurality of windings having a crimped delivery diameter and an expanded implanted diameter, and are oriented in a helical direction of the endovascular device, wherein:

the windings have an undulating pattern comprising struts and loops, the loops being portions of the undulating pattern having a turn of about 180 degrees, wherein each end of a loop is coupled to an end of a strut forming a pair of struts, adjacent loops in the helical direction are axially offset with respect to an axis perpendicular to the lengthwise direction to form a staggered pattern of alignment of adjacent loops, at least one strut is a bent strut comprising a bent pattern along a length of the bent strut in the crimped delivery diameter, wherein the bent pattern comprises first and second bent sections having opposite curvature extending from each end of the bent strut toward a mid-section of the bent strut, and the staggered pattern of alignment of adjacent loops is positioned such that the loops adjacent to the first and second bent sections in the helical direction are positioned to align with and nestle in the first and second bent sections, respectively, in the crimped delivery diameter to form a nestled arrangement.

2. The endovascular device of claim 1, wherein the length of the bent strut comprises a concave curvature and a convex curvature.

3. The endovascular device of claim 2, wherein the first bent section extends from the end of the loop coupled to the pair of struts, the first bent section of the bent strut curving inward toward an opposing strut of the pair and the second bent section curving outward away from the opposing strut of the pair, wherein the bent strut maintains the bent pattern in the crimped delivery diameter and in the expanded implanted diameter such that the first and second bent sections do not substantially straighten during compression of the stent.

4. The endovascular device of claim 2, further comprising a first end ring positioned at the first end and a second end ring positioned at the second end of the continuous component, the first and second end rings extending from the winding adjacent thereto, wherein the first and second end rings are oriented in a circumferential direction and form approximately a right-angled cylinder at lengthwise ends of the endovascular device with respect to the lengthwise direction.

5. The endovascular device of claim 4, wherein each end ring comprises one or more circumferential end bands interconnected in the lengthwise direction and comprises the undulating pattern of loops coupled to the pair of struts, the one or more circumferential end bands comprising struts having variable lengths to produce axially offset loops in the circumferential direction.

6. The endovascular device of claim 5, wherein the staggered pattern of alignment of adjacent loops in the windings forms a uniform stagger, and wherein the axially offset loops in the first and second end rings form a non-uniform stagger such that the loops in the first and second end rings form a scalloped edge.

7. The endovascular device of claim 5, further comprising at least one transition cell enclosed by the undulating pattern of the continuous component and by the undulating pattern of one of the first and second end rings.

8. The endovascular device of claim 5, wherein all of the struts of the first and second end rings are linear struts.

9. The endovascular device of claim 4, wherein each end ring comprises at least one loop having the staggered pattern of alignment and comprises at least one bent strut having the bent pattern such that, as the endovascular device is compressed to the crimped delivery diameter, the at least one loop is positioned to align with and nestle in one of the first and second bent sections of the at least one bent strut adjacent in the circumferential direction.

10. The endovascular device of claim 9, wherein all of the struts of the first and second end rings are bent struts having the bent pattern.

11. The endovascular device of claim 9, wherein at least one of the struts of the first and second end rings is the bent strut having the bent pattern, and wherein remaining struts are linear struts absent the bent pattern.

12. The endovascular device of claim 1, wherein the struts of the pair of struts comprise varying lengths, thereby contributing to forming the staggered pattern of alignment of adjacent loops, the pair of struts comprising a long strut and a short strut such that adjacent struts in the helical direction have the varying lengths, and wherein the long strut has a strut length larger than a strut length of the short strut.

13. The endovascular device of claim 12, wherein at least one of the long strut and the short strut has the bent pattern along the strut length.

14. The endovascular device of claim 13, wherein the long strut of the pair of struts comprises the first and second bent sections, wherein the short strut of the pair of struts is substantially linear and does not comprise the first and second bent sections, wherein the first bent section in the long strut bends inward toward the short strut to form the bent pattern.

15. The endovascular device of claim 13, wherein the long strut and the short strut of the pair of struts each comprises the first and the second bent sections, wherein the first bent section in the long strut and the first bent section in the short strut bends inward toward each other to form the bent pattern.

16. The endovascular device of claim 1, wherein the nestled arrangement is such that the loops adjacent to the first and second bent sections in the helical direction substantially contact the first and second bent sections, respectively, when the endovascular device is compressed to the crimped delivery diameter.

17. The endovascular device of claim 1, wherein at least one strut has a varying width, wherein a width near a mid-section of the strut is smaller than a width near ends of the strut, and wherein a width of the loop is greater than a width of any portion of the strut.

18. The endovascular device of claim 1, wherein each winding of the plurality of windings comprises two interconnected bands including a first band and a second band interconnected to one another to form cells there-between.

19. The endovascular device of claim 18, wherein the first band interconnected to the second band is out-of-phase with the second band in the winding, and wherein non-interconnected adjacent first and second bands in adjacent windings are in-phase.

20. The endovascular device of claim 18, wherein the continuous component further comprises a link interconnecting the two interconnected bands of each winding in the lengthwise direction, wherein the link is a straight connector absent a bend and extends in a gap between the two interconnected bands.

21. The endovascular device of claim 20, wherein, to form the winding, the link connects the first and second bands at loops adjacent in the lengthwise direction forming attachment loops.

22. The endovascular device of claim 21, wherein the attachment loops are the loops at which the gap is smallest, such that the link connects the first and second bands of the winding at the attachment loops on the first and second bands at which the gap is the smallest.

23. The endovascular device of claim 22, wherein the link is positioned at every sixth loop to form the attachment loops and interconnects the first and second bands.

24. The endovascular device of claim 1, further comprising a polymer material electrospun onto the endovascular device, and wherein the polymer material comprises a drug.

25. The endovascular device of claim 1, wherein each winding of the plurality of windings is a single band.

26. The endovascular device of claim 1, wherein all of the struts of the continuous component are bent struts having the bent pattern.

27. The endovascular device of claim 1, wherein at least one of the struts of the continuous component is the bent strut having the bent pattern, and wherein remaining struts are linear struts without the bent pattern.

28. The endovascular device of claim 1, wherein the bent pattern along the length of the bent strut comprises one bent section and one linear section.

29. The endovascular device of claim 1, wherein the endovascular device is one of a peripheral stent, a coronary stent, and a stent-graft device.

* * * * *